US005850002A

United States Patent [19]
Korsmeyer

[11] Patent Number: 5,850,002
[45] Date of Patent: Dec. 15, 1998

[54] ANIMAL MODELS FOR LOSS AND GAIN OF HOX11 FUNCTION

[75] Inventor: Stanley J. Korsmeyer, St. Louis, Mo.

[73] Assignee: Washington University, St. Louis, Mo.

[21] Appl. No.: 712,948

[22] Filed: Sep. 13, 1996

Related U.S. Application Data

[63] Continuation of Ser. No. 231,728, Apr. 20, 1994, abandoned.

[51] Int. Cl.$^6$ .......................... C12N 15/00; A61K 49/00; C07H 21/04
[52] U.S. Cl. ...................... 800/2; 435/172.3; 435/320.1; 536/23.1; 536/23.5; 424/91; 800/DIG. 1; 800/DIG. 4
[58] Field of Search .................................. 800/2; 424/9.1

[56] References Cited

U.S. PATENT DOCUMENTS

| | | | |
|---|---|---|---|
| 4,868,116 | 9/1989 | Morgan et al. | 435/240 |
| 4,980,286 | 12/1990 | Morgan et al. | 435/172.3 |

FOREIGN PATENT DOCUMENTS

| | | | |
|---|---|---|---|
| WO 93/01286 | 1/1993 | WIPO | C12N 15/11 |

OTHER PUBLICATIONS

Connelly et al Exp Cell Res 183: 257, 1989.
Zumar et al Nature 338: 150, 1989.
Roberts et al Blood 82(10): Abstract #332, p. 86a, 1993.
Hatano et al Blood, 1992, Abstr. #1412, p. 355a 34$^{th}$ Annual Meeting.
Balling, R. et al., "Cranofacial Abnormalities Induced by Ectopic Expression of the Homeobox Gene Hox–1,1 in Transgenic Mice," *Cell* 58:367–378 (1989).
Begley, C. G., et al., "The gene SCL is expressed during early hematopoiesis and encodes a differentiation–related DNA–binding motif," *Proc. Natl. Acad. Sci. USA* 86:10128–10132 (1989).
Carter, *Mouse News Lett.* 11:16 (1954)*.
Chaffin, K. E. et al., "Dissection of thymocyte signaling pathways by in vivo expression of pertussis toxin ADP–ribosyltransferse," *EMBO J.* 9:3821–3829 (1990).
Chisaka, O. et al., "Regionally restricted developmental defects resulting from targeted disruption of the mouse homeobox gene hox–1.5," *Nature* 350:473–479 (1991).
Chisaka, O. et al., "Developmental defects of the ear, cranial nerves and hindbrain resulting from targeted disruption of the mouse homeobox gene Hox–1.6," *Nature* 355:516–520 (1992).
Conley, M. E. et al., "The spectrum of the DiGeorge syndrome," *J. Pediatrics* 94:883–890 (1979).
Crist, W. M., et al., "Acute Lymphoid Leukemia," *Clinical Pediatric Oncology* (Editors Fernbach, D.J., et al., pp. 305–336, Mosby Year Book, St. Louis, 1991).
Dear, J. et al., "The HOX11 gene encodes a DNA–binding nuclear transcription factor belonging to a distinct family of homeobox genes," *Proc. Natl. Acad. Sci. USA* 90:4431–4435 (1993).

Dodd, et al., "Spatial Regulation of Axonal Glycoprotein Expression on Subsets of Embryonic Spinal Neurons," *Neurons* 1:105–116 (1988).
Dube, et al., "A Novel Human Homeobox Gene Lies at the Chromosome 10 Breakpoint in Lymphoid Neoplasias With Chromosomal Translocation t(10;14)," *Blood* 78:2996–3001 (1991).
Duboule, D., et al., "The structural and functional organization of the murine HOX gene family resembles that of Drosophila homeotic genes," *EMBO J.* 8:1497–1505 (1989).
Feinberg, et al., "A Technique for Radiolabeling DNA Restriction Endonuclease Fragments to High Specific Activity," *Anal. Biochem.* 132:6–13 (1983).
Gaunt, S.J. et al., *Development*, 107: 131–141 (1989).
Gehring, "Homeo Boxes in the Study of Development," *Science* 236:1245–1252 (1987).
Gossler, et al., "Transgenesis by means of blastocyst–derived embryonic stem cell lines," *Proc. Natl. Acad. Sci. USA* 83:9065–9069 (1986).
Graham, A., et al., "The Murine and Drosophila Homeobox Gene Complexes Have Common Features of Organization and Expression," *Cell* 57:367–378 (1989).
Green, M.C., "A Defect of the Splanchnic Mesoderm Caused by the Mutant Gene Dominant Hemimelia in the Mouse," *Dev. Biol.* 15:62–89 (1967).
Greenburg, F., "What defines DiGeorge anomaly?" *J. Pediatrics*, 11:412–413 (1989).
Guthrie, S., et al., "Neuroectodermal autonomy of Hox–2.9 expression revealed by rhombomere transpositions," *Nature* 356:157–159 (1992).
Hatano, Masahiko, et al., "Deregulation of a Homeobox Gene, HOX11, by the t(10;141) in T Cell Leukemia," *Science* 253:79–82 (1991).
Hunt, P., et al., "Deciphering the Hox Code: Clues to Patterning Branchial Regions of the Head," *Cell* 66:1075–1078 (1991).
Kennedy, et al., "HOX11, a homeobox–containing T–cell oncogene on human chromosome 10q24," *Proc. Natl. Acad. Sci. USA* 88:8900–8904 (1991).

(List continued on next page.)

*Primary Examiner*—Suzanne E. Ziska
*Attorney, Agent, or Firm*—Arnall Glden & Gregory, LLP

[57] ABSTRACT

Genetically engineered animals are described that have lost the expression of a homeobox gene and are missing an organ whose development is regulated by that homeobox gene. Such animals are models for organogenesis and can be used in methods for screening for compounds and gene therapies that restore the function of the missing organ. Other genetically engineered animals are described which express a homeobox gene in cells not normally expressing the gene and exhibit a developmental and/or pathologic condition in those cells. Such animals are models for gain of homeobox function and can be used in methods to screen for compounds and gene therapies that affect the developmental and/or pathologic condition due to the gain of homeobox gene expression.

13 Claims, 9 Drawing Sheets

OTHER PUBLICATIONS

Kessel, M., et al., "Homeotic Transformations of Murine Vertebrae and Concomitant Alteration of Hox Codes Induced by Retinoic Acid," *Cell* 67:89–104 (1991).

Keynes, R., and A. Lumsden, "Segmentation and the Origin of Regional Diversity in the Vertebrate Central Nervous System," *Neuron* 2:1–9 (1990).

Korsmeyer, S. J., "Chromosomal Translocations in Lymphoid Malignancies Reveal Novel Proto–Oncogenes," *Annu. Rev. Immunol.* 10:785–807 (1992).

Kreidberg, J.A., et al., "WT–1 Is Required for Early Kidney Development," *Cell* 74:679–691 (1993).

LeMouellic, H., et al., "Homeosis in the Mouse Induced by a Null Mutation in the Hox–3.1 Gene," *Cell* 69:251–264 (1992).

Lu, M., et al., "The tcl–3 proto–oncogene altered by chromosomal translocation in T–cell leukemia codes for a homeobox protein," *EMBO J.* 10:2905–2910 (1991).

Lufkin, T., et al., "Disruption of the Hox–1.6 Homeobox Gene Results in Defects in a Region Corresponding to Its Rostral Domain of Expression," *Cell* 66:1105–1119 (1991).

Manseau and Schupbach, "The egg came firs, of course!" *Trends Genet.* 5:400–405 (1980).

Mansour, Suzanne, L., et al., "Disruption of the proto–oncogene int–2 in mouse embryo–derived stem cells: a general strategy for targeting mutations to non–selectable genes," *Nature* 336:348–352 (1988).

Marsh, J. Lawrence, et al., "The pIC plasmid and phage vectors with versatile cloning sites for recombinant selection by insertional inactivation," *Gene* 32:481–485 (1984).

McGinnis, W., et al., "Homeobox Genes and Axial Patterning," *Cell* 68:283–302 (1992).

McGuire, Elizabeth A., et al., "Thymic Overexpression of Ttg–1 in Transgenic Mice Results in T–Cell Acute Lymphoblastic Leukemia/Lymphoma," *Molec. Cell. Biol.* 12:4186–4196 (1992).

McGuire, et al., "The t(11;14)(p15;g11) in a T–Cell Acute Lymphoblastic Leukemia Cell Line Activates Multiple Transcripts, Including Ttg–1, a Gene Encoding a Potential Zinc Finger Protein," *Molec. Cell. Biol.* 9:2124–2132 (1989).

McKnight, Steven, "the nucleotide sequence and transcript map of the herpes simplex virus thymidine kinase gene," *Nucleic Acids Res.* 8;5949–5965 (1980).

Mulligan, "The Basic Science of Gene Therapy," *Science* 260:926–932 (1993).

Niehrs, C., et al., "Vertebrate axis formation," *Curr. Opin. Genet. Dev.* 2:550–555 (1990).

Noltenius, H., *Human Oncology: Pathology and Clinical Characteristics*, vol. 8, pp. 1238–1242 (Editors, Noltenius, H., Urban & Schwarzenberg, Baltimore, 1988).

Rabbits, T. H., "Translocations, Master Genes, and Differences between the Origins of Acute and Chronic Leukemias," *Cell* 67:641–644 (1991).

Raju, R., et al., Characterization and developmental expression of Tlx–1, the murine homolog of HOX11, *Mechanisms of Development* 44:51–64 (1993).

Ramirez–Solis, R., et al., "Hoxb–4 (Hox–2.6), Mutant Mice Show Homeotic Transformation of a Cervical Vertebra and Defects in the Closure of the Sternal Rudiments," *Cell* 73:279–294 (1993).

Roberts, Charles Willard Mortimer, "Identification, Characterization, and Gene Ablation of the Oncogene Homeobox SPX (HOX11)," a dissertation presented to the Graduate School of Arts and Sciences of Washington University (May 1995).

Roberts, Charles, W.M., "Hox11 controls the genesis of the spleen," *Nature* 368:747–749 (1994).

Sambrook, et al., *Molecular Cloning: A Laboratory Manual*, Second Edition, pp. 2.33, 9.31–9.62, Cold Spring Harbor Laboratory Press (1989).

Sanchez–Herrero, et al., "Genetic organization of Drosophila bithorax complex," *Nature* 313:108–113 (1985).

Scott, M.P. et et al., "The structure and function of the homeodomain," *Biochim. Biophys. Acta* 989:25–48 (1989).

Stern, C.D., "Vertebrae gastrulation," *Curr. Opin. Genet. Dev.* 2:556–561 (1990).

Swat, W. et al., "Detection of apoptosis of immature $CD4^+8^+$ thymocytes by flow cytometry," *J. Immunol. Meth.* 137:79–87 (1991).

Wakimoto, et al., "Analysis of Larval Segmentation in Lethal Genotypes Associated with the Antennapedia Gene Complex in *Drosophila melanogaster,*" *Dev. Biol.* 81:51–64 (1981).

Waldman, et al., "Sepsis and congenital asplenia," *J. Pediatrics* 90:555–559 (1977).

Wilkinson, D. G., *In situ hybridization: a practical approach*, pp. 75–84 (D. Wilkson, ed.) (IRL Press, 1992).

Wyllie, A. H., "Apoptosis: Cell Death in Tissue Regulation," *J. Pathol.* 153:313–316 (1987).

Zhu, et al., "Systemic Gene Expression After Intravenous DNA Delivery into Adult Mice," *Science* 261:209–211 (1993).

FIG. 2

Human
MEHI.GPHHL.LHPGHAEP ISFG IDQ ILNSPDQGGCMGPA SRLQDGEYGLGCLVGGAYTYGGGG SAA ATG
|||||||||||||||||| |||| ||| |||||||||||| |||||| ||||||||||||||||||||| --- ---
MEHLGPHHLLHPGHAEP ISFG IDQ ILNSPDQGGCMGPA SRLQDGDYGLGCLVGGAYTYGGGG SAAGAG
Murine AGGAGAYGTGGPGGPAGGGG- ACSMGPLTGSYNVNMALAGGPGPGGGGG --- S SGGAGALSAAGV
||| ||||| |||||||||| ||||||||||||||||||||||||||||| --- - ||||||||||
AGGTGAYGAGGPGGPAGGGGACSMGPLPGSYNVNMALAGGPGPGGGGGGGAGGAGAGALSAAGV I RVPAHRPLAGAVAHPQPL ATGLPTVP SVPAMPGVNNLTGLTF PWMESNRRYTKDRFT GHPYQNRTP
| ||||||||||||||||| |||||||| |||| |||||||||||| ||||||| ||||||||| |||||||||
I RVPAHRPLAGAVAHPQPL ATGLPTVP SVPAVPGVNNLTGLTF PWMESNR RYTKDRFT GHPYQNRTP
                                                              ←intron

|←-------- Homeodomain --------|
                                 |-----> |
PKKKKPRTSF TRLQ ICELEKRFHRQKYLASAERAALAKALKMTDAQVKTWFQNRRTKWRRQTAEERE
|||||||||| |||| ||||||||||||||||||||||||||||||||||||||||||||||||||||
PKKKKPRTSF TRLQ ICELEKRFHRQKYLASAERAALAKALKMTDAQVKTWFQNRRTKWRRQTAEERE
                                                              ←intron AERQQANR ILRQLQQEAFQK SLAQPLPADPLCVHNSSLFALQNLQPW SDD STK ITSVTSVA SACE *
|||||||| || |||||||||| |||||||||||||||||||||||||||| ||| ||| |||||||| |||| -
AERQQANR ILLQLQQEAFQK SLAQPLPADPLCVHNSSLFALQNLQPW SDD STK ITSVTSVA SACE

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 333 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Murine ( x i ) SEQUENCE DESCRIPTION: SEQ ID NO:1:

```
Met Glu His Leu Gly Pro His His Leu His Pro Gly His Ala Glu Pro
1               5                   10                  15

Ile Ser Phe Gly Ile Asp Gln Ile Leu Asn Ser Pro Asp Gln Gly Gly
            20                  25                  30

Cys Met Gly Pro Ala Ser Arg Leu Gln Asp Gly Asp Tyr Gly Leu Gly
        35                  40                  45

Cys Leu Val Gly Gly Ala Tyr Thr Tyr Gly Gly Gly Gly Ser Ala Ala
    50                  55                      60

Gly Ala Gly Ala Gly Gly Thr Gly Ala Tyr Gly Ala Gly Gly Pro Gly
65                  70                  75                  80

Gly Pro Gly Gly Pro Ala Gly Gly Gly Gly Gly Ala Cys Ser Met Gly
                85                  90                  95

Pro Leu Pro Gly Ser Tyr Asn Val Asn Met Ala Leu Ala Gly Gly Pro
            100                 105                 110

Gly Pro Gly Gly Gly Gly Gly Gly Gly Gly Ala Gly Gly Ala Gly Ala
        115                 120                 125
```

|   |   |   |   |   |   |   |   |   |   |   |   |   |   |   |
|---|---|---|---|---|---|---|---|---|---|---|---|---|---|---|
| Leu | Ser | Ala | Ala | Gly | Val | Ile | Arg | Val | Pro | Ala | His | Arg | Pro | Leu | Ala |
|   | 130 |   |   |   |   | 135 |   |   |   |   | 140 |   |   |   |   |
| Gly | Ala | Val | Ala | His | Pro | Gln | Pro | Leu | Ala | Thr | Gly | Leu | Pro | Thr | Val |
| 145 |   |   |   |   | 150 |   |   |   |   | 155 |   |   |   |   | 160 |
| Pro | Ser | Val | Pro | Ala | Val | Pro | Gly | Val | Asn | Asn | Leu | Thr | Gly | Leu | Thr |
|   |   |   |   | 165 |   |   |   |   | 170 |   |   |   |   | 175 |   |
| Phe | Pro | Trp | Met | Glu | Ser | Asn | Arg | Arg | Tyr | Thr | Lys | Asp | Arg | Phe | Thr |
|   |   |   | 180 |   |   |   |   | 185 |   |   |   |   | 190 |   |   |
| Gly | His | Pro | Tyr | Gln | Asn | Arg | Thr | Pro | Pro | Lys | Lys | Lys | Lys | Pro | Arg |
|   |   | 195 |   |   |   |   | 200 |   |   |   |   | 205 |   |   |   |
| Thr | Ser | Phe | Thr | Arg | Leu | Gln | Ile | Cys | Glu | Leu | Glu | Lys | Arg | Phe | His |
|   | 210 |   |   |   |   | 215 |   |   |   |   | 220 |   |   |   |   |
| Arg | Gln | Lys | Tyr | Leu | Ala | Ser | Ala | Glu | Arg | Ala | Ala | Leu | Ala | Lys | Ala |
| 225 |   |   |   |   | 230 |   |   |   |   | 235 |   |   |   |   | 240 |
| Leu | Lys | Met | Thr | Asp | Ala | Gln | Val | Lys | Thr | Trp | Phe | Gln | Asn | Arg | Arg |
|   |   |   |   | 245 |   |   |   |   | 250 |   |   |   |   | 255 |   |
| Thr | Lys | Trp | Arg | Arg | Gln | Thr | Ala | Glu | Glu | Arg | Glu | Ala | Glu | Arg | Gln |
|   |   |   | 260 |   |   |   |   | 265 |   |   |   |   | 270 |   |   |
| Gln | Ala | Asn | Arg | Ile | Leu | Leu | Gln | Leu | Gln | Gln | Glu | Ala | Phe | Gln | Lys |
|   |   | 275 |   |   |   |   | 280 |   |   |   |   | 285 |   |   |   |
| Ser | Leu | Ala | Gln | Pro | Leu | Pro | Ala | Asp | Pro | Leu | Cys | Val | His | Asn | Ser |
|   | 290 |   |   |   |   | 295 |   |   |   |   | 300 |   |   |   |   |
| Ser | Leu | Phe | Ala | Leu | Gln | Asn | Leu | Gln | Pro | Trp | Ser | Asp | Asp | Ser | Thr |
| 305 |   |   |   |   | 310 |   |   |   |   | 315 |   |   |   |   | 320 |
| Lys | Ile | Thr | Ser | Val | Thr | Ser | Val | Ala | Ser | Ala | Cys | Glu |   |   |   |
|   |   |   |   | 325 |   |   |   |   | 330 |   |   |   |   |   |   |

( 2 ) INFORMATION FOR SEQ ID NO:2:

( i ) SEQUENCE CHARACTERISTICS:
        ( A ) LENGTH: 330 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapien ( i x ) FEATURE:
        ( A ) NAME/KEY: misc_feature
        ( B ) LOCATION: 200..260
        ( D ) OTHER INFORMATION: /function="homeobox domain"

( i x ) FEATURE:
        ( A ) NAME/KEY: misc_feature
        ( B ) LOCATION: 19..25
        ( D ) OTHER INFORMATION: /function="Hep motif"

( x ) PUBLICATION INFORMATION:
        ( A ) AUTHORS: Hatano,
            Roberts,
            Minden,
            Crist,
            Korslmeyer,
        ( B ) TITLE: Deregulation of a Homeobox gene, HOX11, by
            the t(10;141) in T Cell Leukemia
        ( C ) JOURNAL: Science
        ( D ) VOLUME: 253

(F) PAGES: 79-82
(G) DATE: July 5-1991
(K) RELEVANT RESIDUES IN SEQ ID NO:2: FROM 1 TO 330

(xi) SEQUENCE DESCRIPTION: SEQ ID NO:2:

```
Met Glu His Leu Gly Pro His His Leu Pro Gly His Ala Glu Pro
1               5                   10                  15

Ile Ser Phe Gly Ile Asp Gln Ile Leu Asn Ser Pro Asp Gln Gly
                20              25                  30

Cys Met Gly Pro Ala Ser Arg Leu Gln Asp Gly Glu Tyr Gly Leu Gly
        35              40                  45

Cys Leu Val Gly Gly Ala Tyr Thr Tyr Gly Gly Gly Ser Ala Ala
    50              55                      60

Ala Thr Gly Ala Gly Gly Ala Gly Ala Tyr Gly Thr Gly Gly Pro Gly
65              70                  75                      80

Gly Pro Gly Gly Pro Ala Gly Gly Gly Ala Cys Ser Met Gly Pro
                85                  90                  95

Leu Thr Gly Ser Tyr Asn Val Asn Met Ala Leu Ala Gly Gly Pro Gly
                100             105                 110

Pro Gly Gly Gly Gly Gly Ser Ser Gly Gly Ala Gly Ala Leu Ser Ala
            115             120             125

Ala Gly Val Ile Arg Val Pro Ala His Arg Pro Leu Ala Gly Ala Val
    130             135                 140

Ala His Pro Gln Pro Leu Ala Thr Gly Leu Pro Thr Val Pro Ser Val
145             150                 155                 160

Pro Ala Met Pro Gly Val Asn Asn Leu Thr Gly Leu Thr Phe Pro Trp
            165                 170                 175

Met Glu Ser Asn Arg Arg Tyr Thr Lys Asp Arg Phe Thr Gly His Pro
            180                 185                 190

Tyr Gln Asn Arg Thr Pro Pro Lys Lys Lys Lys Pro Arg Thr Ser Phe
        195             200                 205

Thr Arg Leu Gln Ile Cys Glu Leu Glu Lys Arg Phe His Arg Gln Lys
    210                 215                 220

Tyr Leu Ala Ser Ala Glu Arg Ala Ala Leu Ala Lys Ala Leu Lys Met
225                 230                 235                 240

Thr Asp Ala Gln Val Lys Thr Trp Phe Gln Asn Arg Arg Thr Lys Trp
                245                 250                 255

Arg Arg Gln Thr Ala Glu Glu Arg Glu Ala Glu Arg Gln Gln Ala Asn
            260                 265                 270

Arg Ile Leu Arg Gln Leu Gln Gln Glu Ala Phe Gln Lys Ser Leu Ala
        275                 280                 285

Gln Pro Leu Pro Ala Asp Pro Leu Cys Val His Asn Ser Ser Leu Phe
    290                 295                 300

Ala Leu Gln Asn Leu Gln Pro Trp Ser Asp Asp Ser Thr Lys Ile Thr
305                 310                 315                 320

Ser Val Thr Ser Val Ala Ser Ala Cys Glu
                325
```

(2) INFORMATION FOR SEQ ID NO:3:

(i) SEQUENCE CHARACTERISTICS:
 (A) LENGTH: 276 base pairs
 (B) TYPE: nucleic acid
 (C) STRANDEDNESS: single
 (D) TOPOLOGY: linear (ii) MOLECULE TYPE: cDNA ( i i i ) HYPOTHETICAL: NO ( i v ) ANTI-SENSE: NO ( v i ) ORIGINAL SOURCE:
            ( A ) ORGANISM: Murine ( x i ) SEQUENCE DESCRIPTION: SEQ ID NO:3:

| | | | | | |
|---|---|---|---|---|---|
| ATGGAGCACC | TGGGTCCGCA | CCATCTCCAC | CCGGGCCACG | CGGAGCCCAT | CAGCTTCGGT | 60
| ATCGACCAGA | TCCTCAACCG | CCCCGACCAG | GGCGGCTGCA | TGGGGNNNGC | TTCGCGCCTC | 120
| CAGGATGGAN | NNTATGGCCT | TGGCTGTTTG | GTTGGAGGCG | CCTACACTTA | CGGCGGCGGG | 180
| GGCTCCGCTG | CTGGGGCGGG | GGCCGGGGGC | ACTGGCGCTT | ACGGCGCGGG | TGGCCCAGGT | 240
| GGTCCTGGTG | GTCCGGCGGG | CGGCGGCGGC | GGTGCC | | | 276

( 2 ) INFORMATION FOR SEQ ID NO:4:

( i ) SEQUENCE CHARACTERISTICS:
            ( A ) LENGTH: 71 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Murine ( x i ) SEQUENCE DESCRIPTION: SEQ ID NO:4:

CCGGCTCCTA  CAACGTGAAC  ATGGCCTTGG  CGGGCGGCCC  CGGTCCGGGC  GGCGGCGGCG    60

GTGGCGGGGG  T    71

( 2 ) INFORMATION FOR SEQ ID NO:5:

( i ) SEQUENCE CHARACTERISTICS:
            ( A ) LENGTH: 100 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Murine ( x i ) SEQUENCE DESCRIPTION: SEQ ID NO:5:

CTGAGNGCTG  CAGGGGTGAT  CCGGGTGCCC  GCGCACAGGC  CGCTAGCTGG  AGCTGTGGCC    60

CATCCCCAGC  NCCTGGCCAC  CGGCTTGCCT  ACAGTCCCTC    100

( 2 ) INFORMATION FOR SEQ ID NO:6:

( i ) SEQUENCE CHARACTERISTICS:
            ( A ) LENGTH: 467 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Murine ( x i ) SEQUENCE DESCRIPTION: SEQ ID NO:6:

```
AACAACCTCA  CCNNNCTCAC  CTTTCCCTGG  ATGGAGAGTA  ACCGCAGATA  CACAAAGGAC       60
AGGTTCACAG  GTCACCCCTA  TCAGAACCGG  ACGCCCCTA   AGAAGAAGAA  GCCGCGCACA      120
TCCTTAACGC  GCCTGCAGAT  CTGTGAGCTG  GAAAAGCGCT  TCCACCGCCA  GAAGTACTTG      180
GCTTCGGCGG  AGNGCGCTGC  TCTGGCCAAG  GCGCTCAAAA  TGACCGATGC  GCAAGTAAAA      240
ACCTGGTTCC  AGAACCGGAG  GACGAAATGG  AGGCGACAGA  CAGCAGAGGA  ACGTGAGGCC      300
GAGAGGCAGC  AGGCGAACCG  CATCCTCCTG  CAGCTGCAGC  AGGAAGCCTT  CCAGAAGAGC      360
CTGGCCCAGC  CGCTGCCTGC  AGACCCACTG  TGCGTGCACA  ACTCCTCGCT  CTTCGCCCTG      420
CAGAACCTGC  AGCCGTGGTC  TGACGACTCC  ACCAAAATCA  CCAGCGT                    467
```

( 2 ) INFORMATION FOR SEQ ID NO:7:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Murine ( x i ) SEQUENCE DESCRIPTION: SEQ ID NO:7:

```
CACGTCCGTG  GCTTCGGCCT  GCGAGTGAGG  ACCCAAGGCC  CGTTGAGGAC  TTTCCGGAGA       60
ACCAGAACTC  TCGACACCCT  TTCTGACTNN  NNNNAGGAGG  GAAATGGGGG  GCTTCTCAGC      120
AAGG                                                                      124
```

( 2 ) INFORMATION FOR SEQ ID NO:8:

( i ) SEQUENCE CHARACTERISTICS:
        ( A ) LENGTH: 1988 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapien ( x ) PUBLICATION INFORMATION:
        ( A ) AUTHORS: Hatano,
            Roberts,
            Minden,
            Crist,
            Korslmeyer,
        ( B ) TITLE: Deregulation of a Homeobox gene, HOX11, by
            the t(10;14) in T Cell Leukemia
        ( C ) JOURNAL: Science
        ( D ) VOLUME: 253
        ( F ) PAGES: 79-82
        ( G ) DATE: July 5-1991
        ( K ) RELEVANT RESIDUES IN SEQ ID NO:8: FROM 1 TO 1988

( i x ) FEATURE:
    ( A ) NAME/KEY: misc_feature
    ( B ) LOCATION: 1871..1877
    ( D ) OTHER INFORMATION: /function="sequences that might
        mediate short mRNA half-life"

( i x ) FEATURE:
    ( A ) NAME/KEY: misc_feature
    ( B ) LOCATION: 1907..1912
    ( D ) OTHER INFORMATION: /function="sequences that might
        mediate short mRNA half-life"

( i x ) FEATURE:
    ( A ) NAME/KEY: misc_feature
    ( B ) LOCATION: 1942...1951
    ( D ) OTHER INFORMATION: /function="overlapping poly (A)
        addition signals"

( i x ) FEATURE:
    ( A ) NAME/KEY: misc_feature
    ( B ) LOCATION: 696..878
    ( D ) OTHER INFORMATION: /function="Sequence encoding homeobox
        domain"

( i x ) FEATURE:
    ( A ) NAME/KEY: misc_feature
    ( B ) LOCATION: 153..173
    ( D ) OTHER INFORMATION: /function="Sequence encoding Hep
        motif"

( x i ) SEQUENCE DESCRIPTION: SEQ ID NO:8:

```
CCAGGAGCCG CTGTTGCCTC CCAGCCCCTG CTAGCTGCCC CCCGAGCCGA GCGCAGCGAG      60
CGCCGCCGCC CGGGCCCCCC GGTGGGGCCA GGGCCAGCAT GGAGCACCTG GGTCCGCACC     120
ACCTCCACCC GGGTCACGCA GAGCCCATTA GCTTCGGCAT CGACCAGATC CTCAACAGCC     180
CGGACCAGGG TGGCTGCATG GGACCCGCCT CGCGCCTCCA GGACGGAGAA TACGGCCTTG     240
GCTGCTTGGT CGGAGGCGCC TACACTTACG GCGGCGGGGG CTCCGCGGCC GCGACGGGGG     300
CTGGAGGAGC GGGGGCCTAT GGTACTGGAG GTCCCGGCGG CCCCGGAGGC CCGGCAGGCG     360
GCGGCGGCGC CTGCAGCATG GGTCCTCTGA CCGGCTCCTA CAACGTGAAC ATGGCCTTGG     420
CAGGCGGCCC CGGTCCTGGC GGCGGCGGCG CAGCAGCGG CGGTGCCGGG GCACTCAGCG     480
CTGCGGGGGT AATCCGGGTG CCGGCACACA GGCCGCTCGC CGGAGCCGTG CCCACCCCC     540
AGCCCCTGGC CACCGGCTTG CCCACCGTGC CCTCTGTGCC TGCCATGCCG GGCGTCAACA     600
ACCTCACTGG CCTCACCTTC CCCTGGATGG AGAGTAACCG CAGATACACA AAGGACAGGT     660
TCACAGGTCA CCCCTATCAG AACCGGACGC CCCCAAGAA GAAGAAGCCG CGCACGTCCT     720
TCACACGCCT GCAGATCTGC GAGCTGGAGA AGCGCTTCCA CCGCCAGAAG TACCTGGCCT     780
CGGCCGAGCG CGCCGCCCTG GCCAAGGCGC TCAAAATGAC CGATGCGCAG GTCAAAACCT     840
GGTTCCAGAA CCGGCGGACA AAGTGGAGAC GGCAGACTGC GGAGGAACGG GAGGCCGAGA     900
GGCAGCAAGC GAACCGCATC CTCCGGCAGT TGCAGCAGGA GGCCTTCCAG AAGAGCCTGG     960
CACAGCCGCT GCCCGCTGAC CCTCTGTGCG TGCACAACTC GTCGCTCTTC GCCCTGCAGA    1020
ATCTGCAGCC GTGGTCTGAC GACTCGACCA AAATCACTAG CGTCACGTCG GTAGCGTCGG    1080
CCTGCGAGTG AGCCTGCCCA TTCTGCCCTG TGGGACCCCA GGCCCACTCA GGGGTCACTG    1140
AGGCCTGAGA CCCAGGACTC CTCCCCACCC TCCTGGCCTC AGACTGCACC CAGGAGGGA    1200
ACACTGCCCT CGCACGGCCC CGAAGGGCCC CCACATTTGT GCCGACACTG TTCTCCCTTC    1260
GGTGGAAGAA CTCAAGGGAC AAGGACACGC GCCCCCTCC CAGAGGCGTC CCGCACCTGT    1320
CTGAACTGTT AAGAAATCTG TTTTTGTTTA TTTCATTTTA TTTTAATTTT TAACGTGGGA    1380
TTCAGAGAAA GGCAAGGGAG GTAAGGGAGG AGGAGCTTCT GGGGTCCCCA GGGCTGTCAT    1440
```

```
CTGAATTTGC   CCTGGGAAAC   CCCTTCTCTG   TGACCCACTT   CTCATCACAC   ACATGGAAAC      1500

CCATAGGCCC   ACACACAGGT   GGTGTCACTG   TCCCTCCTGG   TGTCACCCCA   GAGCCACACA      1560

TGGGCATCTA   TGGGAGAGTG   TCAACCAGAC   AGAGGGTCAC   AGTGTTTACA   CTTTGGACCT      1620

TACGATCAGG   CACAGGTCAG   GGGTGACACA   GACTCATCCT   GAACAGCATG   GCACTCCCTC      1680

CAGCACAAAC   ACAAGGTCAT   GGCCACACTG   TGACACACTA   CACCACACAC   AACAGCCAAC      1740

AGCTACAACA   GCCTCACTTG   GTCTGCCAGG   CCCCCACCAC   ACATCCCAGC   CCAATCCAGG      1800

TACGCACAGA   CAGGTTTTCA   CATAAATGCA   GCCCATTTCT   CCAGAACCCA   TTTGAGGGGT      1860

GGGGGGGTGT   TAATTTATGC   ACTTATAAGG   TGTTTTCTGT   GTAACCATTT   TATAAAGTGC      1920

TTGTGTAATT   TATGTGAAAA   AAATAAATAA   AAGCTCCGGA   TCCGGAAAAA   AAAAAAAAA       1980

AAAAAAAA                                                                        1988
```

( 2 ) INFORMATION FOR SEQ ID NO:9:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM:

( x i ) SEQUENCE DESCRIPTION: SEQ ID NO:9:

```
AGAGGAACGT   GAGGCCGAGA                                                         20
```

( 2 ) INFORMATION FOR SEQ ID NO:10:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM:

( x i ) SEQUENCE DESCRIPTION: SEQ ID NO:10:

```
GGATCCCAGA   AGCCTTCCGG                                                         20
```

ANIMAL MODELS FOR LOSS AND GAIN OF HOX11 FUNCTION

This is a continuation of application Ser. No. 08/231,728 filed on Apr. 20, 1994, now abandoned.

BACKGROUND

This invention is generally in the area of homeobox gene function. In particular, animals deficient in orphan homeobox gene function serve as models for organogenesis and are useful in methods for screening and assessing therapies and compounds in treating orphan homeobox gene deficiency.

Various genes have been identified that are involved in the ontogenic process, from polarity generation in the fertilized egg (Manseau, L. J. et al., *Trends Genet.,* 5: 400–405 (1989)) to embryonic axis formation (Niehrs, C. et al., *Curr. Opin. Genet. Dev.,* 2: 550–555 (1990)) to gastrulation (Stern, C. D., *Curr. Opin. Genet. Dev.,* 2: 556–561 (1990)) and spatial pattern formation (McGinnis, W. et al., *Cell,* 68: 283–302 (1992)). A combinatorial gene program appears to pattern the evolutionarily ancient and critical elements of the central nervous system (CNS) and its axial support structures. However, the genetic events that control formation and patterning of individual organs remain principally unknown. Each gene participating in organogenesis could play a role in the development of numerous tissues. Of interest, WT-1 deficient mice fail to develop kidneys but have other abnormalities as well (Kreidberg, J. A. et al., *Cell,* 74: 679–691 (1993)). Alternatively, following regional specification by a gene network, individual genes might be activated which then direct development of a single organ.

The phenomenon of "homeosis" is the aberrant development of one body part or segment of an organism into the likeness of another body part. The best studied examples of homeosis occur in the fruit fly (Drosophila). Genetic analysis revealed that mutation in any of a few dozen genes in the fruit fly can lead to homeotic changes, such as the head segment growing legs where antennae belong (Wakinoto et al., *Dev. Biol.,* 81: 51–64 (1981)), or a second thoracic segment developing in place of an abdominal segment (Sanchez-Herrero et al., *Nature,* 313: 108–113 (1985)). Characterization of these genes revealed that they are involved in controlling segmental identity and that they shared a highly conserved sixty amino acid sequence, now called the homeobox or homeodomain (Gehring, *Science,* 236: 1245–1252 (1987)).

Homeobox genes are evolutionarily conserved transcription factors that act as developmental master switches to control the implementation of segmental or regional identity as well as cell lineage fate choices (Scott, M. P. et al., *Biochim. Biophys. Acta,* 989: 25–48 (1989)). In vertebrates, the tandemly linked Hox genes in four clusters are expressed in overlapping domains along the antero-posterior axis of the embryo (Gaunt, S. J. et al., *Development,* 104: 169–179 (1989)). Many Hox genes display discrete anterior limits of expression that correspond to the segmental boundaries of the rhombomeres in the hindbrain (Wilkinson, D. G. et al., In *In-situ hybridization: a practical approach,* pages 75–84 (1989)). Expression patterns (e.g., Graham, A. et al., *Cell,* 57: 367–378 (1989); Douboule, D. et al., *EMBO J.,* 8: 1497–1505 (1989)), grafting experiments (e.g., Guthrie, S. et al., *Nature,* 356: 157–159 (1992)), ectopic expression (e.g., Balling, R. et al., *Cell,* 58: 367–378 (1989); Kessel, M. et al., *Cell,* 67: 89–104 (1991)), and loss of function experiments (Lufkin, T. et al., *Cell,* 66: 1105–1119 (1991); Chisaka, O. et al., *Nature,* 355: 516–520 (1992); Chisaka, O. et al., Nature, 350: 473–479 (1991); Le Mouellic, H. et al., *Cell,* 69: 251–264 (1992); Ramirez-Solis, R. et al., *Cell,* 73: 279–294 (1993)) suggest that the clustered Hox genes encode a combinatorial system of positional specification along the antero-posterior axis and are critical for implementing overall pattern formation within the hindbrain and branchial arches of the developing embryo (Lufkin et al., 1991; Chisaka et al., 1991; Chisaka et al., 1992; McGinnis et al., *Cell,* 68: 283–302 (1992)). Genes downstream of the clustered Hox genes are largely unknown, and the function of orphan homeobox genes (Scott, M., *Cell,* 73: 279–294 (1993)), i.e., Hox genes located at sites outside the four mammalian Hox clusters, is less well understood than the clustered Hox genes.

Hox11 is an orphan homeobox gene which was originally isolated from the recurrent t(10;14)(q24;q11) breakpoint and translocation found in human T cell acute lymphoblastic leukemia (ALL) (Hatano, M. et al., *Science,* 253: 79–82 (1991); Lu, M. et al., *EMBO J.,* 10: 2905–2910 (1991); Dube, et al., 1991). The translocation does not result in a fusion protein but rather in high level expression of Hox11 protein within T cells. Specifically, the translocation juxtaposes Hox11 with a T cell receptor gene and redirects the expression of the normal Hox11 product to the thymus and thus to circulating thymocytes.

Transgenic mice have been reported in which expression of human Hox11 is redirected to the thymus and T cells. Thymocytes from the transgenic mice die more quickly of apoptosis than thymocytes from their non-transgenic mice. Moreover, thymocytes of the transgenic mice have a significantly increased oncogenic capacity (Hatano, et al., *Blood* 80(suppl.): 355a (1991)). In addition, redirected expression of T cell translocation gene 1 (Ttg-1) to thymocytes in transgenic mice produces a tumorigenic minority population of immature thymocytes whose incidence of tumor development is proportional to the level of redirected expression and thymuses which are significantly larger than controls (McGuire, E. A. et al., *Molec. Cell. Biol.* 12:4186–4196 (1992)).

It is an object of the present invention to provide genetically engineered animal that serve as models for homeobox gene-dependent organogenesis. Such animals, and cells derived from them, are also useful in methods for screening for compounds and/or gene therapies which promote organogenesis.

Another objective is to provide animals in which the expression of a particular homeobox gene has been redirected to cells that normally would not express the gene. Such aberrant redirected homeobox gene expression results in various pathogenic consequences in humans. Accordingly, animals that recapitulate the pathogenic consequence of such aberrant gene expression would serve as models for such human genetic diseases and would be useful in screening for compounds and gene therapies that have a regulatory and/or therapeutic effect on the development and pathology of such diseases.

SUMMARY OF THE INVENTION

Genetically altered animals are produced which possess one or two inactive alleles of a gene that controls the development of a particular organ. Animals deficient in one or both Hox11 alleles can be made using a targeting construct which can recombine with one of the genomic alleles of Hox11 and thereby insert a selectable genetic marker into the allele and disrupt ("knock-out") the coding sequence of the Hox11 gene. Homozygous Hox11$^{-/-}$ animals completely lack a spleen and thus can serve as animal models for organogenesis and can also be used for examining morphogenetic development of a single organ, to screen for compounds and therapies that promote or supplement deficiencies in organ development and for use in determining immunologic and hematopoietic contributions of the spleen.

Genetically engineered animals which redirect the expression of a particular homeobox gene, such as human Hox11, recapitulate the developmental and pathologic consequence of such aberrant gene expression in humans. These animals can be used in methods for screening for compounds and gene therapies that have a therapeutic effect on the developmental and/or pathologic conditions associated with such aberrant genetic expression in humans.

BRIEF DESCRIPTION OF THE DRAWINGS

FIG. 2 shows a comparison of the amino acid sequences of murine (Sequence ID No. 1) and human (Sequence ID No. 2) Hox11 proteins as deduced from nucleic acid sequence data.

DETAILED DESCRIPTION OF THE INVENTION

I. Animal Models for Organogenesis

Figures 1A, 1B:
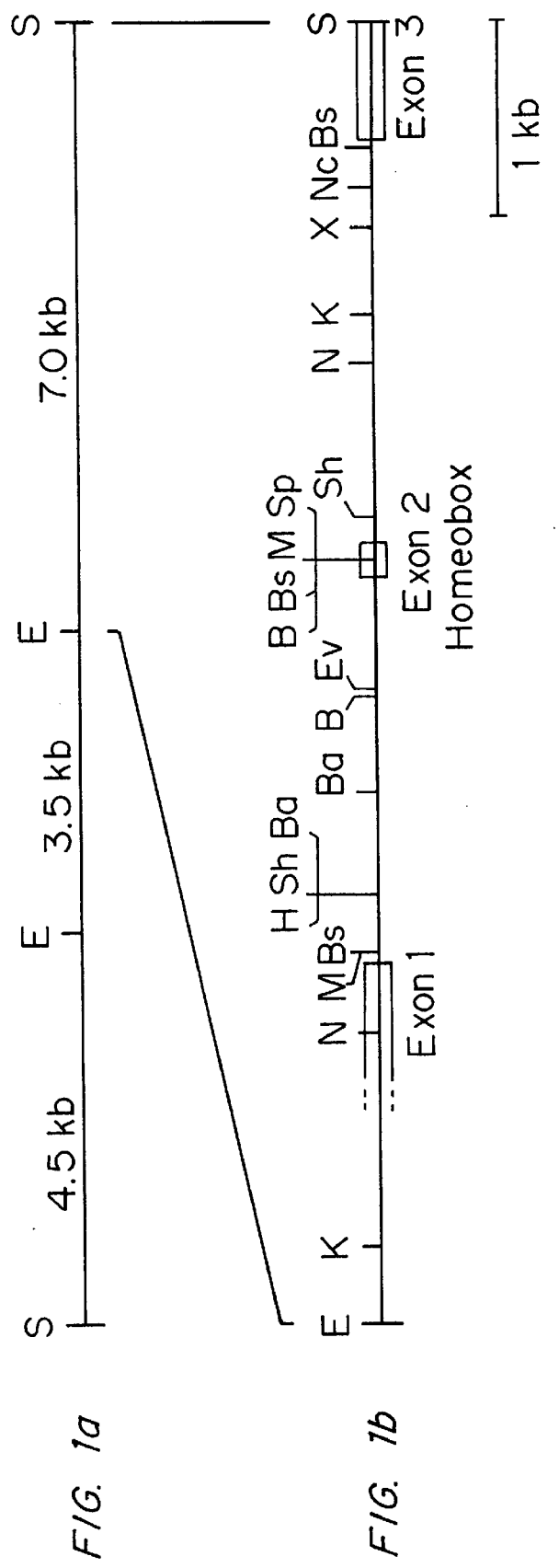
FIG. 1a shows schematically a restriction endonuclease map of a phage clone containing the mouse genomic Hox11 gene.
FIG. 1b shows schematically a restriction endonuclease map of a 7 kilobase (kb) subclone of the phage clone containing the Hox11 gene and the relative position of Hox11 exons 1, 2 and 3. Open boxes indicate exons. Incomplete box indicates that exon 1 contained the 5' untranslated region of Hox11 which was not sequenced. Restriction sites: B, BglII; Ba, BamHI; Bs, BssHI; E, EcoRI; Ev, EcoRV; H, HindIII; K, KpnI; M, MscI; N, NarI; Nc, NcoI; S, SalI; Sh, SphI; Sp, SpeI; X, XbaI. The SalI sites are from the phage arms and are not found in the genomic DNA.

An effective animal model for deficiency in a gene that controls organogenesis must possess both alleles stably inactivated so that throughout embryogenesis one or more tissues cannot revert to a functional wild-type allele.

One method of generating animals with an altered genotype is gene targeting, as described by Mansour et al. (*Nature*, 336: 348–352 (1988)), in which homologous recombination of newly introduced DNA sequence (i.e., the targeting sequence or construct) and a specific targeted DNA sequence residing in the chromosome results in the insertion of a portion of the newly introduced DNA sequence into the targeted chromosomal DNA sequence. This method is capable of generating animals of any desired genotype, and is especially useful for disrupting (i.e., to "knock out") a specific chromosomal gene sequence by inserting a selectable marker into the gene. To knock out a genomic gene, a cloned fragment must be available and intron-exon boundaries within the fragment defined (Mansour et al., 1988). Typically, the targeting construct contains a selectable marker such as Neo (neomycin resistance, see Mansour et al., 1988) flanked by sequences homologous to the chromosomal target DNA, and beyond one of these flanking sequences the herpes simplex virus thymidine kinase gene (HSV-TK, McKnight et al., *Nucleic Acids Res.*, 8: 5949–5965 (1980)). The targeting construct is introduced, e.g., by electroporation, into embryo-derived stem (ES) cells where homologous recombination results in an insertion of the Neo marker, but not the HSV-TK gene, into the targeted chromosomal DNA sequence. The altered ES cells are neomycin resistant and HSV-TK⁻ and so are able to grow in the presence of both G418 and gancyclovir antibiotics, whereas random insertions contain the HSV-TK gene and are sensitive to gancyclovir (Mansour et al., 1988). Positive ES clones can then be microinjected into blastocysts to generate germ-line chimeras, and bred to obtain progeny that are homozygous for the knock out gene. Such general methods of generating knock out animal have been demonstrated using mice. However, genes in other animals such as rats, guinea pigs, gerbils, hamsters, and rabbits, may also be used as long as sufficient DNA sequence data are available to make an appropriate targeting construct to knock out the gene of interest.

DNA Sequence for Orphan Homeobox Gene Hox11

The human Hox11 was originally isolated from the recurrent t(10;14)(q24;q11) chromosomal breakpoint found in human T cell acute lymphoblastic leukemia (ALL). The human cDNA Hox11 gene sequence and the corresponding amino acid sequence of the encoded open reading frame (ORF) are shown in Sequence ID Nos. 8 and 2, respectively. Probes were generated from the human cDNA sequence and used to isolate the murine genomic Hox11 gene sequence from a murine Balb-c genomic DNA library consisting of MboI partially-digested genomic DNA cloned into the bacteriophage lambda-based EMBL3 cloning vector (Sambrook et al., *Molecular Cloning: A Laboratory Manual, second ed.,* page 2.33, Cold Spring Harbor Laboratory Press 1989).

A 7 kilobase (kb) EcoRI-SalI mouse genomic DNA fragment was isolated which restriction mapping and sequence analysis revealed to contain three exons encoding the entire mouse Hox11 ORF (FIG. 1). The amino acid sequence of the mouse Hox11 ORF (Sequence ID No. 1) is taken as the amino acid sequence of the mouse Hox11 protein and was deduced from partial nucleic acid sequencing of the genomic clone and the work of Dear, J. et al., *Proc. Natl. Acad. Sci. USA,* 90: 4431–4435 (1993) (Sequence ID Nos. 3, 4, 5, 6 and 7).

The first exon contains the 5' untranslated (UT) region and encodes the first 180 amino acids of the protein. The second exon encodes 66 amino acids and contains virtually all of the homeodomain. The amino acid sequence of the murine Hox11 protein as defined by the ORF is shown in Sequence ID No. 1. A comparison of the amino acid sequences of the human Hox11 and the murine Hox11 proteins is shown in FIG. 2.

Targeting Construct For Homologous Recombination With Murine Genomic Hox11

By designing and using an appropriate targeting construct, it is possible to specifically target and knock out a particular allele in the genome of an animal.

Figure 3:
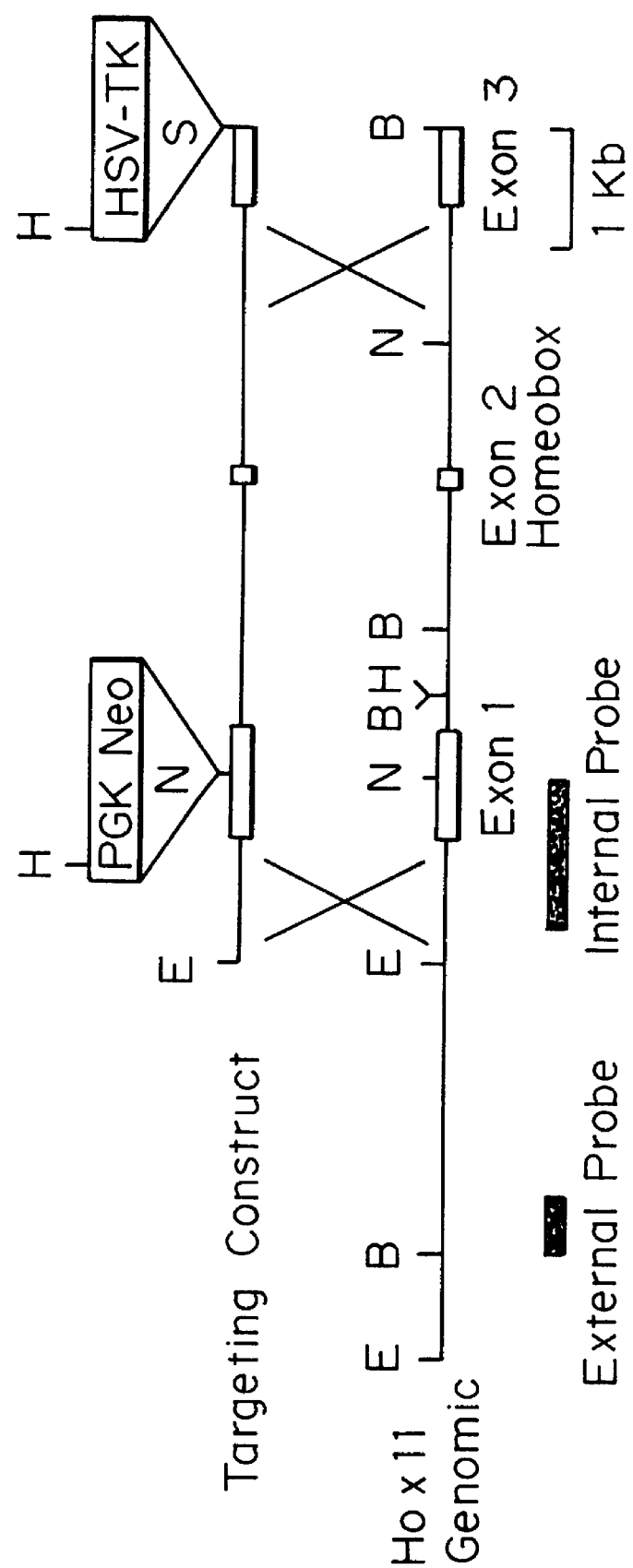
FIG. 3 shows schematically the targeting construct used to inactivate ("knock out") a genomic mouse Hox11 gene by homologous recombination (indicated by the two sets of crossed lines) and the relative position of external and internal probes used to confirm insertion of targeting construct sequences. PGK-Neo, a neomycin resistance gene driven by a PGK promoter, inserted into a copy of exon 1 of Hox11; HSV-TK, a herpes simplex virus thymidine kinase gene inserted at the 3' end of the coding sequence of exon 3 of Hox11; B, BamHI; E, EcoRI; H, HindIII; N, NarI; S, SalI.

A targeting construct used to knock out the Hox11 gene in mice is shown schematically in FIG. 3. This construct was made by cloning a 6.75 kb SalI-EcoRI fragment of the murine genomic Hox11 gene sequence into plasmid pBLUESCRIPT™ KS (Stratagene, La Jolla, Calif.). The EcoRI cohesive end of the fragment is upstream from exon 1 of Hox11 and the SalI cohesive end of the fragment is located at the downstream end of exon 3, i.e., 3' to the exon 3 coding sequence. This fragment contained the entire ORF of Hox11 within the three exons of the gene. Two NarI sites were present in this fragment. Partial digestion with NarI was followed by size separation by electrophoresis through a 0.5% agarose gel to enrich for plasmid that had been cut only once with NarI. A PGK-Neo cassette was modified by ligating ClaI linkers which are compatible with NarI cohesive ends of the plasmid. The PGK-Neo sequence containing the ClaI linkers was then cloned into the NarI site of the plasmid located at the codon for amino acid 53 of the ORF. An HSV-TK gene was inserted into the SalI end of the fragment, i.e., at the 3' end of exon 3 coding sequence.

Electroporation of embryonic stem cells

D3 murine embryonic stem (ES) cells ($3 \times 10^7$ cells) were electroporated with 30 µg of targeting construct in a volume of 0.8 ml HeBSS (HEPES buffered normal saline) at 275 V, 200 µF in a BTX 300 (BTX, San Diego, Calif.) with a flat pack electrode. $3 \times 10^6$ cells were then plated on irradiated neomycin-resistant primary murine embryonic fibroblasts (MEF). At 24 hours, 500 µg/ml G418 and 2 µM gancyclovir were added for selection. Colonies were picked beginning at day 9, dispersed and transferred to 24 well plates containing irradiated MEF. When colonies appeared, they were picked, dispersed into a single cell suspension and 75% of the cells frozen. The remaining 25% were expanded for DNA in 24 well plates on gelatin alone. Homologous recombinants were confirmed with both BamHI and HindIII digestion and hybridization with an "external" and "internal" probes. The external probe is a 0.5 kb BamHI-BglII fragment which is located 2.0 kb upstream of the EcoRI site in the targeting construct (see FIG. 3). The internal probe is a 1.1 kb KpnI-NarI fragment within the targeting construct (see FIG. 3).

The external probe hybridized to a 6.3 kb HindIII germ-line fragment (i.e., wild-type allele) and a 5.6 kb rearranged (disrupted allele) fragment following homologous recombination due to a HindIII site within the inserted PGK-Neo gene.

The internal probe contains part of exon I and was used to confirm homologous recombinants. Hybridization with this probe ensured that there was only one integration site in each ES clone.

Microinjection of Blastocysts with disrupted Hox11 allele

Seven of 163 G418-gancyclovir double resistant clones had undergone homologous recombination. ES clones with a disrupted Hox11 allele were microinjected into C57BL/6 blastocysts and reimplanted into 2.5 day pseudo-pregnant females to generate chimeric offspring. High color coat chimeras transmitted the disrupted Hox11 allele (knock out gene) through the germline.

Analysis of Progeny

Heterozygous mice were completely normal and matings resulted in the expected Mendelian frequency of homozygous (Hox11$^{-/-}$) mice which grew into adulthood and were externally indistinguishable from wild-type littermates. Southern blots of BamHI digested genomic DNA from the progeny of an Hox11$^{+/-}$ X Hox11$^{+/-}$ cross indicated that all combinations of the Hox11 alleles were born. DNA from mice heterozygous for an inactivated Hox11 allele (+/−), homozygous for inactivated Hox11 alleles (−/−) and wild-type littermates (+/+) were compared. The upper band corresponds to sequence outside Hox11 hybridized by external probe and the lower band corresponds to sequence of Hox11 hybridized by internal probe. −/− mice did not express the lower band; +/+ mice did not express the upper band. Both males and females were fertile.

Analysis for Hox11 expression in normal and Hox11$^{-/-}$ knock out embryos

1. In situ hybridizations

In order to focus the search for defects in the homozygous Hox11$^{-/-}$ knock out mice, tissues that normally express Hox11 were closely examined. Staging of embryos was according to the criteria of Theiler (*The House Mouse: Development and Normal Stages from Fertilization to 4 weeks of Age* (Springer-Verlag, Berlin, 1989). Whole-mount in situ hybridization was carried out according to Wilkinson, D. G. In *In situ hybridization: a practical approach*, pages 75–84 (D. Wilkson, ed.) (IRL Press, 1992), incorporated herein by reference, using a 450 nucleotide probe beginning 3' of the homeobox coding sequence and continuing into the 3' untranslated region and bordered by the upstream sequence 5'AGAGGAACGTGAGGCCGAGA3' (Sequence ID No. 9) and downstream sequence 5'GGATCCCA-GAAGCCTTCCGG3' (Sequence ID No. 10). Probes were synthesized using digoxigenin-UTP (Boehringer-Mannheim) and a transcription kit (Stratagene, La Jolla, Calif.). Abdominal organs of embryos older than E11.5 (i.e., 11.5 days old embryos) were dissected free prior to hybridization to maximize probe penetration.

Figure 5A:
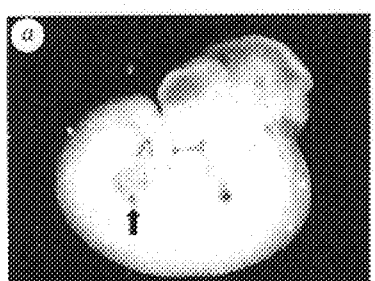
FIG. 5a shows expression of Hox11 within splanchnic mesoderm (arrow) of an E11.5 (11.5 day old embryo) whole mount embryo as identified by in situ hybridization with a Hox11 probe. Expression of Hox11 also visible in the hindbrain and at the third branchial cleft.

Previous RNA in situ hybridization studies revealed that Hox11 is normally expressed within portions of the developing branchial arches and hindbrain (Raju, R. et al., *Mechanisms of Development*, 44: 51–64 (1993)). Hox11 is initially expressed at E8.5 (i.e., day 8.5 of embryogenesis) in the developing muscle plates of branchial arches 1, 2 and 3, and subsequently in the motor nuclei that innervate them, i.e., cranial nerves V, VII, and IX respectively. Additionally, Hox11 is normally expressed in the vestibulocochlear, geniculate, and a portion of the trigeminal ganglia, the surface ectoderm of the first bronchial arch, and in the ventral portion of the 3rd branchial cleft. As shown in FIG. 5*a*, beginning at E11.5, Hox11 is also expressed at a single site in the abdomen within a portion of the splanchnic mesoderm.

In situ hybridization of Hox11$^{-/-}$ embryos revealed no sites of expression indicating that the Hox11 transcript was disrupted. Extensive dissections revealed that the pharyngeal and mastication muscles derived from the branchial arches were present and anatomically normal.

2. Whole-mount immunostaining

In order to examine the structure of cranial ganglia which normally express Hox11, whole mount immunostaining was performed with MAb 2H3 which binds a 155 kilodalton (kd) intermediate neurofilament protein and stains sensory ganglia. (Dodd et al., *Neuron*, 1: 105–116 (1988)). Embryos were fixed in 4% paraformaldehyde in phosphate buffered saline (PBS) for 24 hours at 4° C., then washed three times in PBS for 60 minutes. Endogenous peroxidase was blocked by an overnight wash in 0.05% hydrogen peroxide, 1% Triton X-100, in PBS. Embryos were washed three times in 1% Triton X-100 in PBS for 60 minutes, then incubated with MAb 2H3 diluted 1:1 with 10% newborn calf serum, 1% Triton X-100, 0.02% azide in Basal Medium Eagles (GIBCO/BRL, Gaithersburg, Md.) under gently rocking at 4° C. for three days. The embryos were then washed three times in 1% normal goat serum, 1% Triton X-100 in PBS (PBSGT) followed by an incubation with peroxidase-conjugated goat antimouse IgG Fc (Sigma, St. Louis, Mo.) diluted 1:100 in PBSGT overnight at 4° C. After washing as before, embryos were washed twice in 0.5M Tris, pH 7.6 for 30 minutes. The embryos were then equilibrated in a solution of the color substrate 3,3'-diaminobenzidine (DAB, BioRad, Hercules, Calif.): 0.5 mg DAB/ml in Tris, pH 7.6 for 3 hours in the dark at 4° C. for 1 to 5 minutes. The color reaction was carried out in 0.02% hydrogen peroxide, 0.5 mg DAB/ml Tris 0.5M, pH 7.6 at 4° C. for 1 to 5 minutes and stopped by three washes in PBS for 60 minutes.

The results of the whole mount immunostaining indicated that the morphology and position of the cranial ganglia appeared identical in wild-type and Hox11$^{-/-}$ mice.

Hox11-deficient animals lack a spleen

Figure 4A:
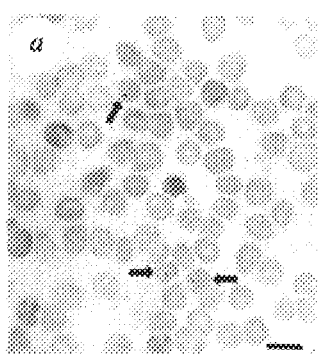
FIG. 4a shows erythrocytes from Hox11$^{-/-}$ mice containing Howell-Jolly bodies (arrows).
Figure 4B:
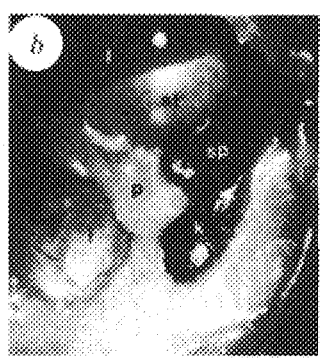
FIG. 4b shows internal organs of a Hox11$^{+/+}$ mouse.
Figure 4C:
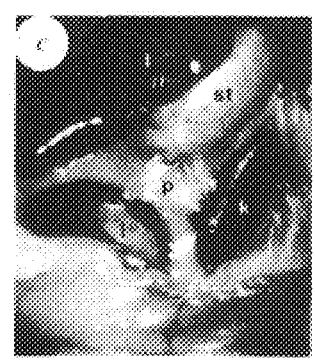
FIG. 4c shows internal organs of a Hox11$^{-/-}$ lacking a spleen. Abbreviations: sp, spleen; k, kidney; p, pancreas, l, liver; i, intestine.

Complete blood counts revealed that while Hox11$^{-/-}$ mice possessed normal numbers of red blood cells, they had increased numbers of white blood cells which included both neutrophils and lymphocytes (White Blood Cell count of $16.5 \pm 5.1 \times 10^3$ cells/mm$^3$ in Hox11$^{-/-}$ versus $8.6 \pm 2.5$ in normals p<5×10$^{-4}$). Flow cytometry indicated that the B cell and T cell profile was normal in thymus, lymph node and peripheral blood. Hox11$^{-/-}$ mice demonstrated numerous erythrocytes containing nuclear fragments known as Howell-Jolly bodies (see FIG. 4*a*). These abnormal cells are found most frequently in asplenia (Koyama, Acta. *Haematol. Jpn.*, 23: 20 (1960)). Abdominal dissection of each of 34 Hox11$^{-/-}$ mice examined revealed the complete absence of the spleen (compare FIG. 4*b* (Hox11$^{+/+}$) and FIG. 4*c* (Hox11$^{-/-}$)). All other internal organs in the Hox11$^{-/-}$ mice were normal in appearance and position.

Hox11 expression in normal and Hox11$^{-/-}$ developing embryos

Figure 5B:
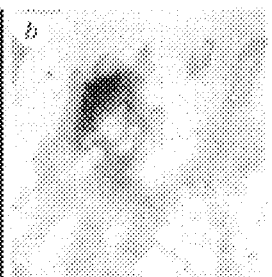
FIG. 5b shows a transverse section through the splanchic mesoderm of the E11.5 embryo hybridized with the Hox11 probe and the beginning of condensation at the site of the splenic primordium.
Figure 5C:
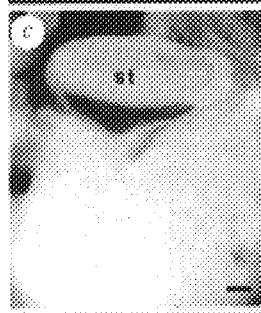
FIG. 5c shows abdominal organs from an E12.5 embryo hybridized with the Hox11 probe and the strong positive hybridization signal of the splenic primordium attached to the dorsal side of the stomach.
Figure 5D:
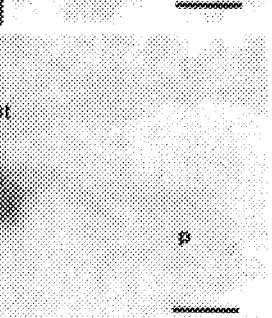
FIG. 5d shows a transverse section through the E12.5 embryo of FIG. 5c hybridized to the Hox11 probe showing expression of Hox11 in the mesenchymal cells of the splenic primordium.
Figure 5E:
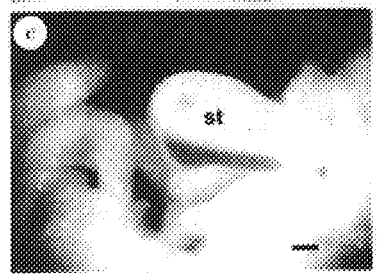
FIG. 5e shows expression of Hox11 in splenic primordium of E13.5 embryo as detected by hybridization with the Hox11 probe.
Figure 5F:
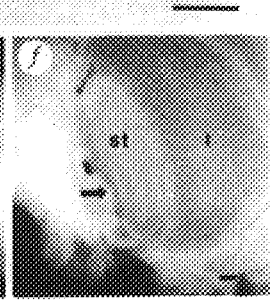
FIG. 5f shows markedly weaker expression of Hox11 in spleen (arrow) of E14.5 compared to earlier time points (compare FIGS. 5d and 5e) as detected by hybridization with the Hox11 probe. Abbreviations: st, stomach; p, pancreas; l, liver.

Since ablation of Hox11 in the knock out animals resulted in asplenia, Hox11 expression was examined in the abdomen of normal embryos from E8.5 through E16.5 (embryogenesis days 8.5 through 16.5). Hox11 was expressed in a highly localized portion of the splanchnic mesoderm beginning at E11.5 (FIG. 5*a*). During the eleventh day of embryonic development, cells that express Hox11 appeared to be emigrating from splanchnic mesoderm and beginning to condense in a small mass on the dorsolateral margin of the future stomach (FIG. 5*b*). This mesoderm continues to express Hox11 as it proliferates to form the definitive spleen. By E12.5, the splenic primordium has increased in size and was visible as a ridge of cells expressing Hox11 on the dorsal aspect of the stomach (FIG. 5*c*). Sections through this area revealed that the spleen had partially separated from the stomach and that Hox11 was specifically expressed in the mesenchymal cells of the spleen (FIG. 5*d*). Hox11 was expressed in the developing spleen through E13.5 (FIG. 5*e*), but was down regulated thereafter (FIG. 5*f*). The first hematopoietic cells to populate the spleen do not appear until E15.5 (Rugh, R. *In The Mouse: Its Reproduction and Development* (Oxford University Press, New York, 1990)).

Previously, the first recognized histologic evidence of splenic development was the condensation and proliferation of mesenchymal tissue recorded at E12.5 (Green, M. C., *Dev. Biol.*, 15: 62–89 (1967)). Consequently, the expression of Hox11 at E11.5 identifies mesodermal cells destined to form the spleen prior to the appearance of a morphologically recognizable organ.

Figure 6A:
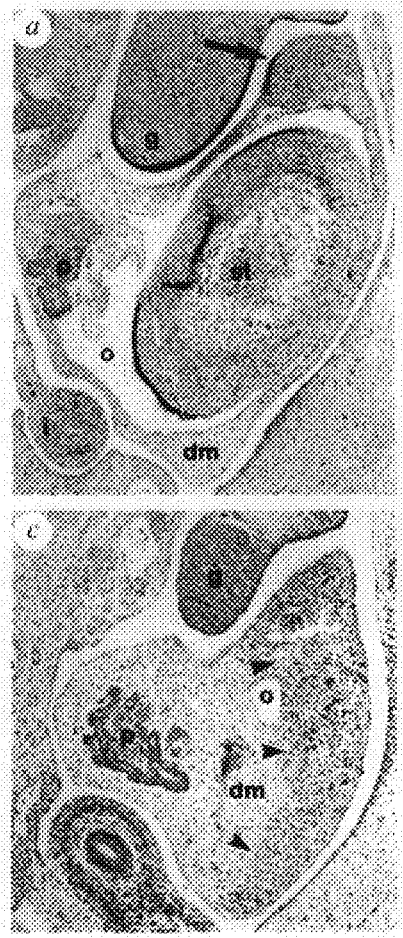
FIG. 6a shows a transverse section through an E13.5 normal embryo demonstrating the splenic (arrow) and pancreatic primordia within the dorsal mesogastrium.
Figure 6B:
FIG. 6b shows a transverse section through an E13.5 Hox11$^{-/-}$ embryo revealing the lack of a splenic primordium.
Figure 6C:
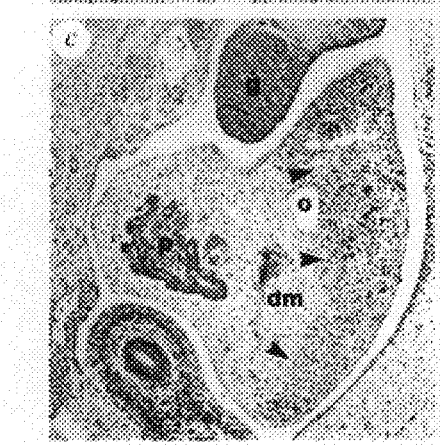
FIG. 6c shows a transverse section of an E12.5 normal embryo through the dorsal mesogastrium just caudal to the stomach. Arrowheads indicate the boundary of condensation of mesenchymal cells destined to form the spleen.
Figure 6D:
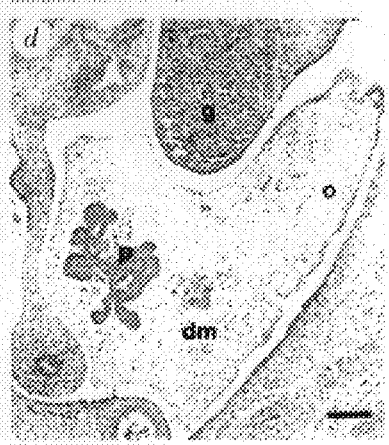
FIG. 6d shows a transverse section through an E12.5 Hox11$^{-/-}$ embryo demonstrating a lack of condensation and organization of mesenchymal cells within the dorsal mesogastrium and a lack of tissue between the sac of the omentum (o) and the lateral edge of the dorsal mesogastrium compared to a normal embryo (compare FIG. 6c). dm, dorsal mesogastrium; g, gonad; i, intestine; o, sac of omentum; p, pancreas; st, stomach.

The mesogastrium, a precursor of the adult mesentery, is derived from mesoderm and gives rise to the pancreas and spleen. Sections through an E13.5 wild-type mouse revealed an obvious splenic primordium within the dorsal mesogastrium (see FIG. 6*a*). However, serial sections through an E13.5 Hox11$^{-/-}$ embryo revealed no evidence for a splenic primordium (FIG. 6*b*). Development of the pancreas and stomach proceeded normally in the Hox11$^{-/-}$ mice. More caudal sections through earlier, E12.5 wild type embryos identified cellular organization and mesenchymal cell condensation at the site where the spleen forms (FIG. 6*c*). In contrast, serial sections through E12.5 Hox11$^{-/-}$ mice revealed no identifiable organization or condensation and indicated that the effect of Hox11 disruption was already manifest by E12.5 (see FIG. 6*d*). Thus, elimination of Hox11 results in a specific, localized defect in the mesodermal cells normally destined to form the spleen, while other structures within the mesogastrium develop normally.

Uses for knock out animals lacking organs

Because Hox11$^{-/-}$ embryos fail to develop even a detectable remnant of a spleen, Hox11 must control a downstream gene program responsible for the genesis of the spleen. Thus, the orphan homeobox Hox11 gene is alone sufficient for patterning the development of the spleen. Other organs including the pancreas, kidneys, liver, heart, and lungs may be expected to be under the control of a single homeobox gene. Consequently, the capacity to regulate or deliver by gene therapy the single homeobox gene responsible for each organ could have an important therapeutic benefit, i.e., regeneration of functioning organ tissue. For example, particular gene therapy with homeobox genes and/or proteins could be utilized to regenerate one or both kidneys in severe renal failure, a pancreas in diabetes mellitus or severe pancreatitis with pancreatic failure, and a spleen in individuals lacking a spleen due to congenital absence or surgical splenectomy.

Genetically altered animals, such as the Hox11$^{-/-}$ knock out mice described above, are thus useful to screen for compounds and therapeutic regimens that regulate the development of individual organs and/or supply the function that the missing organ normally would provide. For example, compounds or therapeutic regimens can be administered to Hox11$^{-/-}$ mice, at various selected concentrations and for selected periods of time, and the mice monitored for the development of spleen tissue. Such compounds include molecules and compounds that may regulate organogenic gene expression and include homeobox genes or other genes, other nucleic acid molecules that may serve regulatory functions and/or the proteins encoded by homeobox genes or other genes that regulate organogenesis.

Genetically engineered knock out animals that lack a particular organ are useful in assessing gene therapies. One or more copies of a wild-type gene or other nucleic acid construct, known or presumed to be critical for development of the missing organ, can be delivered to a specific site in such knock out animals, and the animals monitored over time to determine whether the missing organ is regenerated. For example, in the case of Hox11$^{-/-}$ animals, one or more copies of the wild-type Hox11 gene or other functionally equivalent nucleic acid construct can be delivered to selected cells in the abdomen, and the animals monitored for formation of spleen tissue.

Methods and systems of delivering compounds and genetic constructs to animals

A number of compositions and methods are currently available to administer compounds, including proteins and nucleic acid molecules, to cells of an animal or human. For example, plasmid and eukaryotic viral vectors may be used to express a particular gene in cells depending on the preference and judgment of the skilled practitioner (see, Sambrook et al., Chapter 16). Furthermore, a number of viral and nonviral vectors are being developed that enable the introduction of nucleic acid sequence in vivo (see, e.g., Mulligan, *Science,* 260: 926–932 (1993); U.S. Pat. No. 4,980,286; U.S. Pat. No. 4,868,116; incorporated herein by reference). Other delivery systems that may be used include using liposomes which encapsulate compounds. Recently, a delivery system was developed in which nucleic acid is encapsulated or adhered to cationic liposomes which can be injected intravenously into a mammal (e.g., Zhu et al., *Science,* 261: 209–211 (1993)). Other delivery systems include topical or tissue surface delivery systems such as Pluronic™ (polypropylene oxide-polyethylene oxide block copolymer) gel which is liquid at 4° C. and solid at room temperature (PCT WO 93/01286). Other biodegradable polymers can be substituted for the Pluronics™ such as polylactic acid and polyglycolic acid copolymers, polyethylene, and polyorthesters which can be used to form implants for controlled release of compounds, proteins or nucleic acid constructs directly to a tissue where gene expression and/or organ development is desired.

II. Animal Models for Redirecting Expression of Human Hox11 to Developing Thymocytes As noted above, the orphan homeobox human Hox11 gene was previously identified as a chromosomal translocation event at the t(10;14)(q24;q11) recurrent breakpoint in T cells of ALL patients. One result of such translocations is to deregulate a series of transcription factors principally intended for other cell types (Rabbits, T. H. *Cell* 67, 641–644 (1991); Korsmeyer, S. J. *Annu. Rev. Immunol.* 10, 785–807 (1992); Begley, C. G., Aplan, P. D., Denning, S. M., Haynes, B. F., Waldmann, T. A., and Kirsch, I. R. *Proc. Natl. Acad. Sci. USA* 86, 10128–10132 (1989)). An animal that recapitulates such translocation events or otherwise redirects expression of a gene to a new tissue or organ is useful for elucidating the developmental and/or pathological effects of such redirected gene expression on the tissue or organ in which the redirected expression occurs. Furthermore, such animals are useful for screening for compounds and gene therapies that have a regulatory or therapeutic effect on the developmental and/or pathological condition of tissues or organs of animals and humans in which such redirected gene expression has been found. For example, an animal that recapitulates the translocation of Hox11 expression from the hindbrain to the thymus would be useful in studying the developmental and pathological effects on the thymus and T cells. Such animals can be used for screening for compounds and gene therapies that have a regulatory and/or therapeutic effect on thymocyte development and/or ALL pathology.

Transgene construction

In order to redirect expression of a selected gene using transgenic methods, a promoter should be used in the design of the transgene construct that will ensure that the selected gene, once integrated into the animal genome, will be expressed preferentially or specifically in the cells to which expression is redirected.

For example, in order to recapitulate the effect of the t(10;14) translocation, a transgene construct was made in which the human Hox11 cDNA sequence (Sequence ID No. 8) was inserted 3' to a promoter active in thymocytes, e.g., the lck proximal promoter (lck$^{Pr}$, see, Chaffin, K. E. et al., *EMBO J.,* 9: 3821–3829 (1990)). The human Hox11 cDNA possessing the ORF for the 330 amino acid protein was ligated into the BamHI site of an lck-hGH expression vector between the lck proximal promoter and the human growth hormone (hGH) gene to generate the lck$^{Pr}$-Hox11 transgene construct. Production of Transgenic Mice.

Transgenic animals can be generated by standard methods in which a genetic construct is introduced directly into an embryo that results in a viable fetus. The most common methods of such direct introduction of gene sequences are microinjection of embryos and injection of embryonic stem cells into blastocysts. The procedures for manipulation of the rodent embryo and for microinjection of DNA are described in detail in Hogan et al., *Manipulating the mouse embryo,* (Cold Spring Harbor Laboratory, Cold Spring Harbor, N.Y., 1986), the teachings of which are incorporated herein. Other small animals such as rats, guinea pigs, gerbils, hamsters, and rabbits can also be similarly manipulated to obtain transgenic animals. Embryonic stem (ES)

cells can be manipulated using the method of Gossler, et al., Proc. Natl. Acad. Sci. USA, 83: 9065–9069 (1986), the teachings of which are incorporated herein.

Typically, when microinjected embryos are to be used to produce transgenic mice, female mice six weeks of age are induced to superovulate, e.g., with a 5 IU injection (0.1 cc, ip) of pregnant mare serum gonadotropin (PMSG, Sigma, St. Louis, Mo.), followed 48 hours later by a 5 IU injection (0.1 cc, ip) of human chorionic gonadotropin (hCG, Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline (DPBS) with 0.5% bovine serum albumin (BSA, Sigma). Surrounding cumulus cells are removed with hyaluronidase (e.g., 1 mg/ml). Pronuclear embryos are then washed and placed in a buffer such as Earle's balanced salt solution containing 0.5% BSA (EBSS) in a 37.5° C. incubator with a humidified atmosphere at 5% $CO_2$, 95% air until the time of microinjection.

For Hox11 transgenic mice, linear lck$^{Pr}$-Hox11 transgene construct DNA was prepared and microinjected into the pronuclei of (C57BL/6×C3H) F1 mouse zygotes. Transgenic mice were generated as described by Hogan et al., *Manipulating the mouse embryo*, (Cold Spring Harbor Laboratory Press, Cold Spring Harbor, N.Y., 1986). Minigene constructs were resuspended in microinjection buffer (5 mM Tris, pH 7.4, 0.25 mM EDTA, 5 mM NaCl) to a final concentration of 2–5 ng/µl. C57BL/6×C3H/He F1 females were superovulated by sequential intraperitoneal injections of 5 U of pregnant mare serum (Sigma Chemical Co., St. Louis, Mo.) and 5 IU human chorionic gonadotropin (Sigma) and mated with fertile F1 males. Single cell embryos were harvested the following day using Brinster's BMOC-3 media (GIBCO/BRL, Grand Island, N.Y.). Cumulus cells were removed by brief incubation in 300 µg/ml hyaluronidase. Pronuclei were microinjected with approximately 1–2 picoliters of minigene construct DNA, and two cell embryos were reimplanted the following day into pseudopregnant ICR outbred female mice.

Detection and analysis of founders

Tail biopsies and mouse organs were digested overnight at 55° C. in 2.5 ml of extraction buffer (50 mM Tris-HCl, pH 8.0, 100 mM EDTA, 100 mM NaCl, 1% sodium dodecyl sulfate) containing 1 mg of proteinase K (Beckman, Fullerton, Calif.). DNA was ethanol precipitated after four phenol-chloroform extractions. DNA pellets were washed twice with 80% ethanol, dried and resuspended in 10 mM Tris (pH 7.4), 0.1 mM EDTA. Restriction endonuclease digestion by BamHI, PstI, or EcoRI, agarose gel electrophoresis, and Southern blotting were done using standard techniques (Sambrook et al., *In Molecular Cloning: A Laboratory Manual*, second ed., pages 9.31–9.62 (Cold Spring Harbor Laboratory Press, Cold Spring Harbor, N.Y., 1989)). The human Hox11 cDNA (Hatano, M. et al., Science, 253: 79–82 (1991)) was utilized as a probe. The DNA probe was labelled with $^{32}P$ by random hexanucleotide priming (Feinberg et al., *Anal. Biochem.*, 132: 6–13 (1983)). Filters were hybridized overnight at 42° C. in the presence of 10% dextran sulfate, 50% formamide 4X SSC, 1X Denhardt's solution, 10 µg/ml salmon sperm DNA. Blots were washed twice with 0.1% sodium dodecyl sulfate at 55° C. and exposed to X-ray film at −70° C. to obtain autoradiographs.

Transgenic animals expressing human Hox11 develop small thymuses

Transgenic (Tg) lck$^{Pr}$-Hox11 lines which express human Hox11 in the most immature thymocytes exhibited a developmental block at the CD4$^-$8$^-$ to CD4$^+$8$^+$ transition. Dissection of animals indicated that five Tg lines demonstrated a small thymus (Sm #1, 8, 22, 23, 64a) in which the total number of thymocytes was less than 50% of normal. T cell development was markedly altered in these Tg lines. The percentage of CD4$^-$8$^-$ double negatives (DN) and CD4$^+$8$^+$ double positive (DP) thymocytes can be determined by flow cytometry analysis of antibody stained thymocytes. The absolute number of CD4$^-$8$^-$ double negative (DN) thymocytes was normal while CD4$^+$8$^+$ double positive (DP) thymocytes and both CD4$^+$8$^-$ and CD4$^-$8$^+$ mature thymocytes were dramatically reduced. The total number of T cells in spleen and lymph node was also decreased. Furthermore, the thymuses of the small thymus-transgenic (Sm-Tg) animals were observed to be markedly dysplastic with numerous apoptotic bodies and, thus, resembled the human congenital immunodeficiency DiGeorge anomaly (Conley, M. E. et al., *J. Pediatrics*, 94, 883–890 (1979); Greenburg, F. *J. Pediatrics*, 11, 412–413 (1989)). In contrast, seven other Tg lines displayed a normal sized thymus (Nm #26, 30, 45, 47, 61, 64b, 68) and no abnormalities of T cell populations in the thymus, spleen or lymph nodes. There was no correlation between the overall level of transgene expression in the thymus and thymocyte number.

An S1 nuclease protection assay (Hatano, M. et al., Science, 253: 79–82 (1990)) was used to determine Hox11 expression. Transgene RNA expression was detected with an S1 protection assay utilizing a radiolabeled anti-sense human Hox11 cDNA probe. A β2 microglobulin mouse anti-sense genomic fragment probe was used as an internal control probe for RNA content and quality. Twenty µg of RNA were hybridized overnight with 1×10$^5$ counts per minute of each labeled probe at 50° C., digested with S1 nuclease, and electrophoresed. The results of this assay indicated that Sm-Tg lines expressed high levels of Hox11 in DN thymocytes while Nm-Tg lines did not. This also indicates that Hox11 only exerts its maximal effect if expressed at the most immature stages of thymocyte development.

T cell maturation appeared arrested at the DN to DP transition in the Sm-Tg lines. Yet, there was no excess accumulation of DN thymocytes. This indicated that cell death occurred during T cell maturation.

Hox11-dependent cell death in thymocytes of transgenic animals

Figure 7:
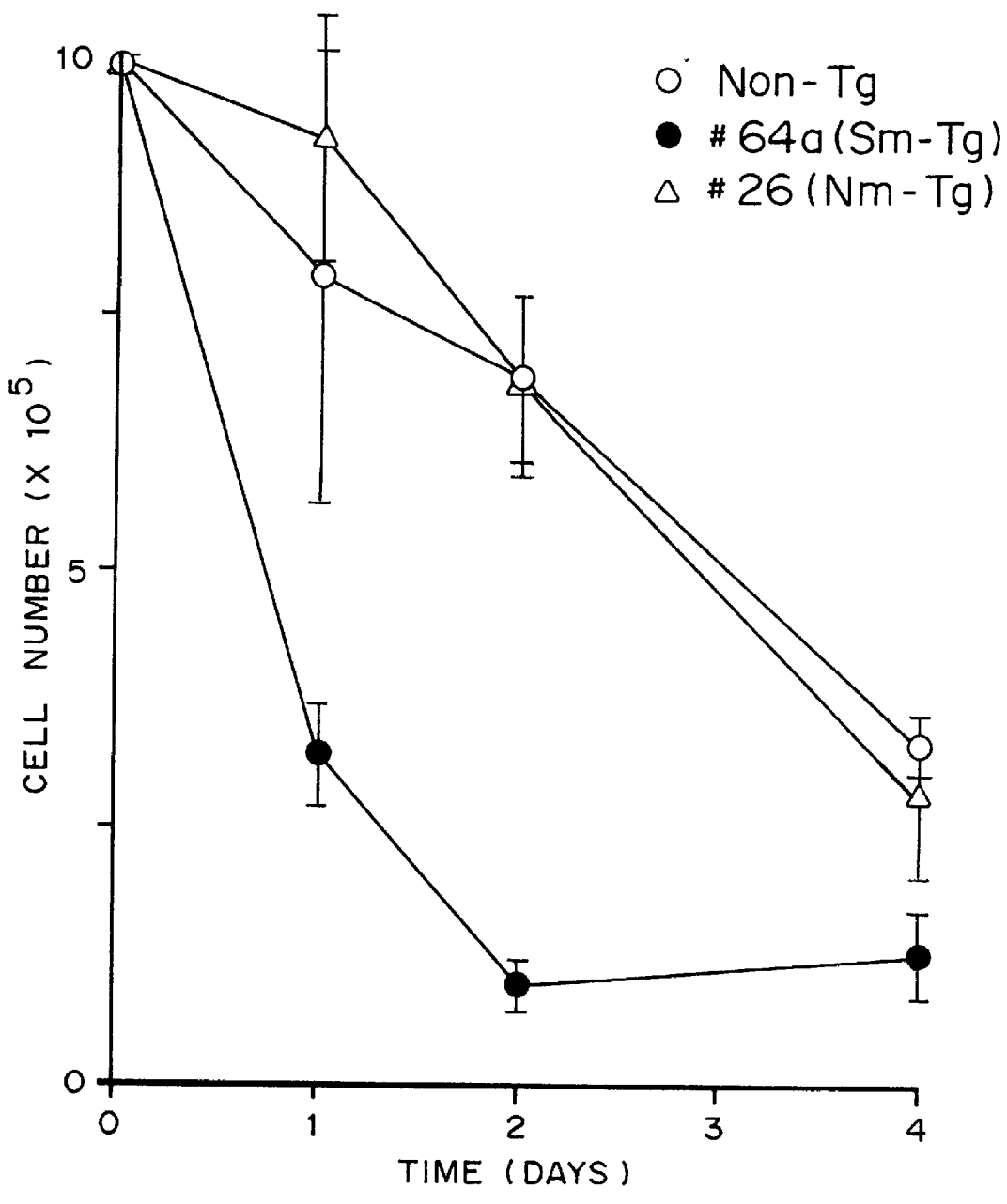
FIG. 7 shows in vitro survival of thymocytes plotted as the mean viable cell number±SD in triplicate cultures.

Cell death was assayed by in vitro survival of thymocytes. As shown in FIG. 7, when placed in culture, thymocytes from Sm-Tg lines died more rapidly than Nm-Tg or non-Tg.

To determine whether or not the increased rate of cell death of thymocytes was due to apoptosis a standard assay for DNA fragmentation, a characteristic of apoptosis, was used (e.g., Wyllie, A. H. *J. Pathol.*, 153: 313–316 (1987)). Thymocytes isolated from Sm-Tg #22 and non-Tg (NT) controls were cultured for 6 hours in RPMI 1640 with 5% FCS, or with 100 µM dexamethasone (NT:Dex). DNA was isolated from each sample and size fractionated by agarose gel electrophoresis. Thymocytes of Sm-Tg lines exhibited increased DNA fragmentation typical of apoptosis.

Aberrant cell cycles in transgenic animals with small thymuses

A cell cycle analysis of Tg thymocytes was performed to determine whether aberrations in thymocyte maturation and cell death were accompanied by abnormalities in cell cycle progression. Thymocytes were isolated from three animals each of lines Sm-Tg #22 and #26 and Nm-Tg #26 as well as three non-Tg mice. Cells were stained with anti-CD3 monoclonal antibody followed by FITC conjugated goat anti-hamster IgG. Stained cells were permeabilized with 0.2% saponin and DNA was detected with propidium iodide as described previously. Flow cytometry was performed on FACScan and data was analyzed by Cellfit software. Percentage of S and G2/M phase in total thymocytes, $CD3^-$, $CD3^{lo}$, $CD3^{med}$ and $CD3^{hi}$ populations are presented as the mean of three independent experiments. The results are shown in the Table 1 below.

TABLE 1

Cell Cycle Analysis of Transgenic Thymocytes

|  | Total | | $CD3^-$ | | $CD3^{lo}$ | | $CD3^{med}$ | | $CD3^{hi}$ | |
| --- | --- | --- | --- | --- | --- | --- | --- | --- | --- | --- |
|  | S | G2/M | S | G2/M | S | G2/M | S | G2/M | S | G2/M |
| Non-Tg | 9.4 | 1.5 | 13.2 | 1.4 | 9.4 | 2.6 | 3.5 | 1.0 | 3.2 | 0.6 |
| Sm#22 | 24.1 | 3.0 | 17.1 | 1.3 | 26.3 | 9.9 | 32.9 | 5.8 | 10.1 | 3.0 |
| Sm#64a | 17.3 | 1.7 | 6.9 | 0.6 | 19.4 | 2.4 | 28.1 | 3.2 | 13.9 | 2.5 |
| Nm#26 | 9.2 | 0.9 | 9.2 | 0.6 | 10.4 | 2.3 | 4.4 | 0.9 | 2.6 | 0.6 |

As shown in Table 1 above, normal thymocytes displayed a progressive decline in the percentage of cells in S phase as they mature from $CD3^-$ (13.2%) to $CD3^{lo}$ to $CD3^{med}$ to $CD3^{hi}$ (3.2%) stages as shown in Table I below. No abnormalities of cell cycle were noted in the Nm-Tg mice which only express Hox11 in the later stages of T cell development. In contrast, Sm-Tg mice demonstrated a marked increase in thymocytes within the S, G2, and M phases during maturation.

Figure 8A:
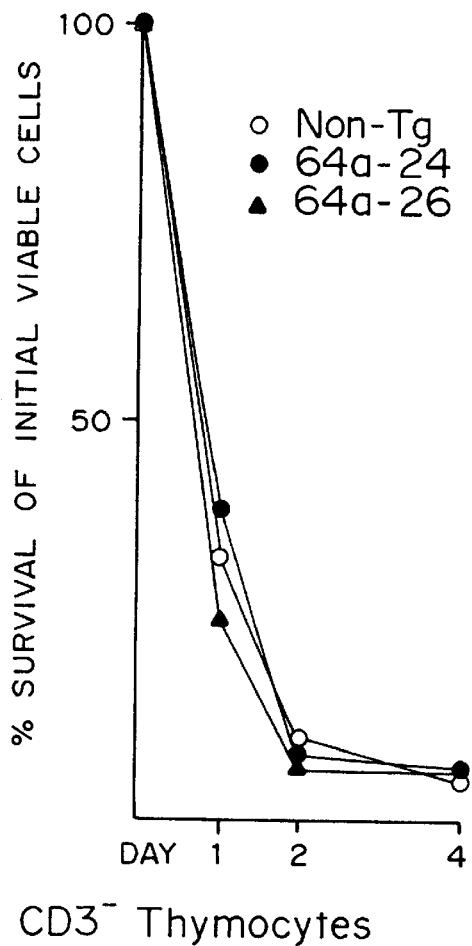
FIG. 8a shows in vitro survival of CD3$^-$ and FIG. 8b shows in vitro survival of CD3$^{med}$ thymocytes from transgenic animals having small thymuses, i.e., Sm-Tg #64a-24, #64a-26, and non-transgenic littermates, i.e., non-Tg.
Figure 8B:
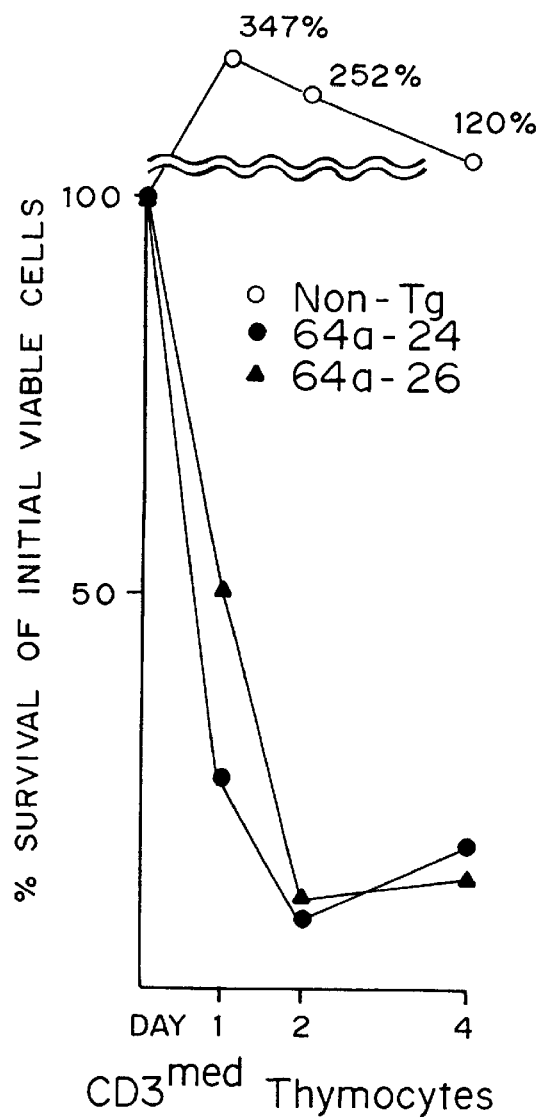

Because approximately 30% of $CD3^{med}$ cells of Sm-Tgs were in S-phase compared to 3.5% in non-Tg mice, the survival of CD3 subsets of thymocytes in vitro was examined (FIGS. 9a and 9b). Thymocytes isolated from Tg and non-Tg littermates were cultured at the initial concentration of $1\times10^6$ per ml in RPMI 1640 with 5% FCS. The number of surviving cells was determined by trypan blue exclusion. In some experiments, after in vitro culture cells were stained with biotinylated anti-CD3 monoclonal antibody followed by streptavidin-RED613. Live cells were determined by flow cytometry by gating according to forward and side scatter (Swatt, W. et al., J. Immunol. Meth., 137: 79–87 (1991)). The percentage of $CD3^-$, $CD3^{lo}$, $CD3^{med}$, and $CD3^{hi}$ high populations was determined by consort 30 software. In FIGS. 9a and 9b, surviving cells are indicated as the percent of the initial viable cells. The $CD3^-$ thymocytes decreased at comparable rates in Sm-Tg (64a-24 and 64a-26 in FIG. 8a) and non-Tg mice. Both cell death and maturation contribute to the loss of this subset. Similar results were obtained for Sm-Tg #22 cells. In contrast, the number of viable $CD3^{med}$ cells initially increased upon culture of normal non-transgenic thymocytes (Non-Tg in FIG. 8b). However, in comparison to both Non-Tg and Nm-Tg thymocytes, the cycling $CD3^{med}$ thymocytes from Sm-Tgs died rapidly (FIG. 8b). These findings indicate that immature thymocytes ($CD3^-$, $CD4^-8^-$) upon maturation to $CD3^+$ stages demonstrate accelerated cell cycle progression which results in apoptotic cell death and a marked decrease in the number of mature T cells.

Histological analysis of Sm-Tg animals

Tissue samples were prepared for histological analysis by fixing the tissue sample in 10% neutral buffered formalin and staining with hematoxylin and eosin. Histology of the pre-malignant Sm-Tg thymus from 6 week old mice revealed a disorganized architecture with no defined cortex or medulla, and numerous mitotic figures as well as apoptotic bodies. These histological data indicate that accelerated cell division and cell death of Sm-Tg thymocytes also occur in vivo. Such histology is similar to that observed in the human congenital immunodeficiency, DiGeorge anomaly, which is characterized by thymic hypoplasia and craniofacial abnormalities (Conley, M. E. et al., J. Pediatrics, 94: 883–890 (1979); Greenburg, F. J. Pediatrics, 11: 412–413 (1989)). Thus, with T cell maturation, Hox11 expression in the transgenic animal results in cell cycle progression and programmed cell death of T cells, and furthermore, transgenic lines which exhibit increased death and decreased numbers of thymocytes progress to T cell malignancy. These results indicate the observed Hox11 oncogenesis results from a disordered cell cycle which promotes genomic instability i.e., mutations that alter normal growth as well as apoptosis.

Oncogenic potential of redirected Hox11 expression

Figure 9:
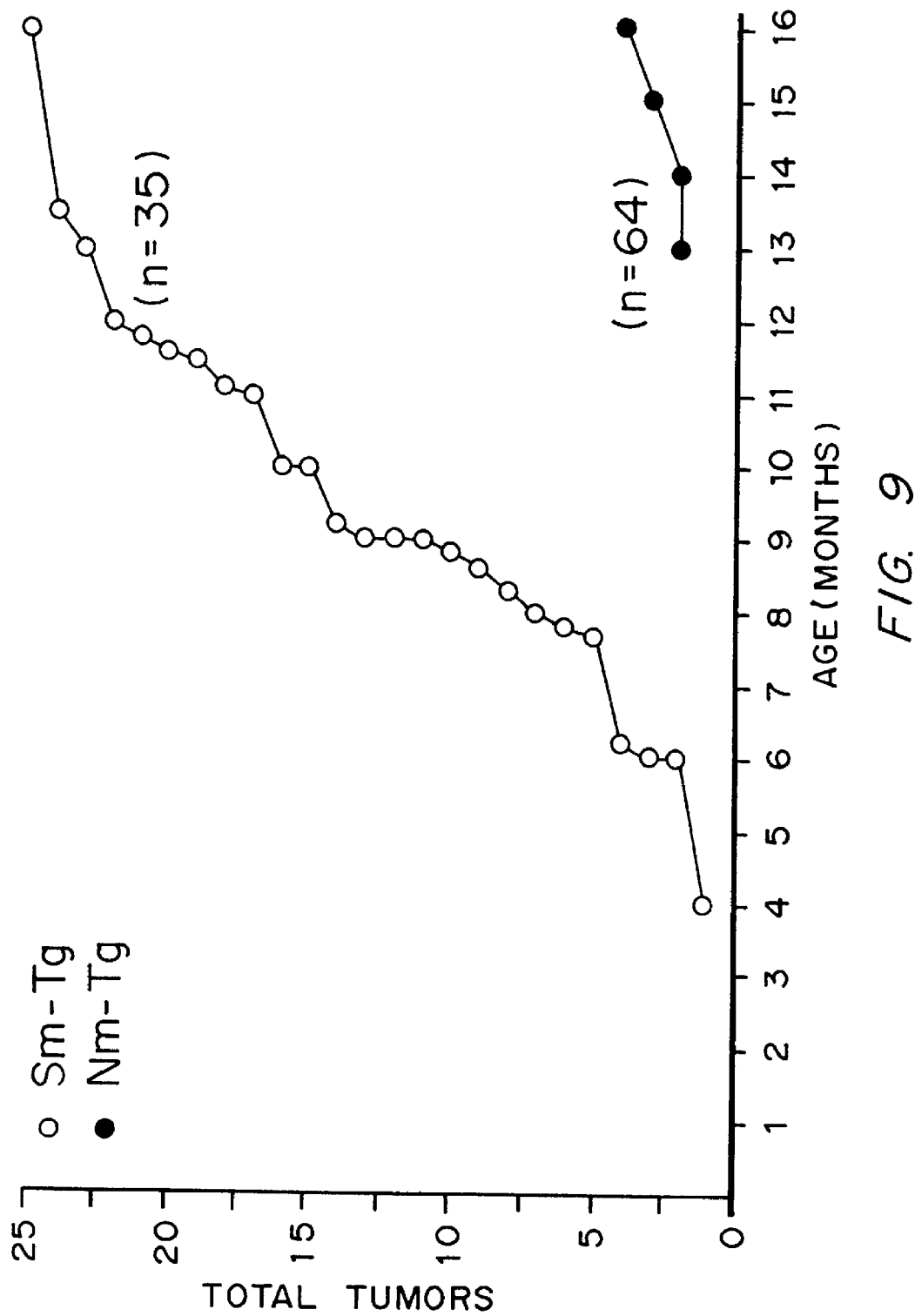
FIG. 9 shows the incidence of T cell lymphoma/leukemia in lck$^{Pr}$-Hox11 Tg mice. A cohort of thirty-five (n=35) Sm-Tg mice from lines #1, #8, #22, #23, #64a and sixty-four (n=64) Nm-transgenic mice from lines #26, #30, #45, #47, #64b, #67 and #68 were followed. Malignant lymphocytes were also frequently found in blood, kidney and liver. No tumors developed in age matched non-Tg littermates.

To assess the oncogenic potential of redirected Hox11 expression, a cohort of thirty-five Sm-Tg mice (Sm-Tg lines #1, #8, #22, #23, #64a) and sixty-four Nm-Tg mice (Nm-Tg lines #26, #30, #45, #47, #64b, #67, #68) were followed. Malignant lymphocytes were frequently found in blood, kidney and liver of the Sm-Tg mice, whereas no tumors developed in age matched non-Tg littermates. Histology of premalignant Sm-Tg 122, 6 week old thymus and of thymic origin T cell lymphoblastic lymphoma demonstrates that T cell acute lymphoblastic lymphoma/leukemia in thymus tissue of Sm-Tg preferentially developed in mice of Sm-Tg lines (23/35, 65.7%) compared to Nm-Tg lines (5/64, 7.8%), as shown in FIG. 9.

The results indicate that Tg lines which demonstrate increased S phase, accelerated cell death and decreased numbers of thymocytes progressed to neoplasia at a high rate. Tumor histology was typical of a lymphoblastic lymphoma of thymic origin similar to the mediastinal masses seen in humans with T cell ALL (Crist, W. M. et al. In Clinical Pediatric Oncology (eds. Fernbach, D. J. et al.) 305–336 (Mosby Year Book, St. Louis, 1991); Noltenius, H. Human Oncology: Pathology and Clinical Characteristics, Vol. 8, pages 1238–1242 (ed. Noltenius, H.) (Urban & Schwarzenberg, Baltimore, 1988)). The normal architecture of the thymus was replaced by lymphoblasts with numerous mitotic figures and scattered tingible body macrophages. In addition, occasional tumors appeared to originate in mesenteric lymph nodes. All tumors were clonal as assessed by T cell receptor gene rearrangement (McQuire et al., Molec. Cell. Biol., 9: 2124–2132 (1989)) and compatible with the mean age of onset of tumors at 9 months. Tumors in Sm-Tgs were not restricted to a single stage of T cell development ($CD4^-8^-$:3 tumors; $CD4^+8^+$:6 tumors; $CD4^+8^-$:4 tumors; $CD4^-8^+$:1 tumors.

Uses for animal models of redirected homeobox gene expression

Proteins of homeobox families have been shown to direct pattern formation in embryogenesis or to regulate cell type specification by activating target genes (Scott, M. P. et al., Biochem. Biophys. Acta, 989: 25–48 (1989); Keynes, R. et al., Neuron 2: 1–9 (1990); Hunt, P. et al., Cell, 66: 1075–1078 (1991); Chisaka, O., et al., Nature, 350: 473–479 (1991); Chisaka, O. et al., Nature, 355: 516–520 (1992); and LeMouellic, H. et al., Cell, 69: 251–264 (1992)). Animals which recapitulate the redirection of a homeobox gene can be used as models for the developmental and/or pathological consequence of such redirected gene expression. Thus, such animals can be used in methods for screening for compounds or for assessing regimens or gene therapies that affect the developmental and/or pathological conditions that result from such redirected gene expression. The transgenic animals described above which express Hox11 in the thymus and developing thymocytes and exhibit pathologic consequences similar to those observed in the t(10;14)(q24;q11) chromosomal translocation in humans, are an example of such useful animal models.

The transgenic mice which expressed Hox11 in their thymuses developed a high incidence of acute T cell lymphoblastic lymphoma/leukemia indicating a primary oncogenic role for redirected Hox11. The Hox11 Tg lines prone to neoplasia demonstrate a novel premalignant phenotype. An apparent maturational arrest at the DN to DP thymocyte transition reflects a developmental stage specific cell death. These data suggest that Hox11 induces cell cycle acceleration initiating both cell death, which can be viewed as protective, and genomic instability that leads to the acquisition of secondary mutations. The Hox11 transgenic mice can serve as a model for the inter-relationship involving cell cycle, cell death and neoplasia. Accordingly, these animals are useful in methods for screening for compounds, regimens, and gene therapies that affect the developmental and/or pathologic conditions of the t(10;14)(q24;q11) chromosomal translocation in humans, including T cell ALL.

In addition to the guidance and examples described above, it will be appreciated that various changes and modifications can be made without departing from the invention.

We claim:

1. A transgenic mouse homozygous for Hox11 gene inactivation, wherein the Hox11 gene is inactivated by insertion of a heterologous nucleic acid sequence into the Hox11 gene via homologous recombination, wherein the inactivation of the Hox11 gene prevents expression of the Hox11 gene, and whereby the mouse is asplenic.

2. A transgenic mouse having integrated into its genome the human Hox11 gene operably linked to a promoter specifically active in thymocytes,
   wherein expression of the Hox11 gene in the thymus cells of the transgenic mouse renders the thymus of the transgenic mouse smaller than the thymus of mice not expressing the human Hox11 gene.

3. The transgenic mouse of claim 2 wherein T cells of the transgenic mouse exhibit a developmental block at the $CD4^-8^-$ to $CD4^+8^+$ transition.

4. The transgenic mouse of claim 2 wherein the thymus of the transgenic mouse is dysplastic.

5. The transgenic mouse of claim 2 wherein the total number of thymocytes in the thymus of the transgenic mouse is less than 50% of the total number of thymocytes in the thymus of mice not expressing the human Hox11 gene.

6. The transgenic mouse of claim 2 wherein the total number of T cells in the spleen and lymph nodes of the transgenic mouse is less than the total number of T cells in the spleen and lymph nodes mice not expressing the human Hox11 gene.

7. The transgenic mouse of claim 2 wherein thymocytes cultured from the transgenic mouse die more rapidly than thymocytes cultured from mice not expressing the human Hox11 gene.

8. The transgenic mouse of claim 2 wherein thymocytes of the transgenic mouse exhibit neoplasia.

9. A method for screening for a compound, wherein the compound affects a developmental and/or pathological condition due to expression of the human Hox11 gene in the thymus or T cells that do not normally express the human Hox11 gene, the method comprising:

administering the compound to the transgenic mouse of claim 2, and monitoring the mouse for a change in the developmental and/or pathological condition.

10. The method of claim 9 wherein the developmental and/or pathological condition is the production of dysplastic T cells, and wherein the transgenic mouse is monitored for a change in the production of dysplastic T cells.

11. The method of claim 9 wherein the developmental and/or pathological condition is the production of neoplastic T cells, and wherein the transgenic mouse is monitored for a change in the production of neoplastic T cells.

12. The method of claim 9 wherein the developmental and/or pathological condition is that the total number of thymocytes in the thymus of the transgenic mouse is less than 50% of the total number of thymocytes in the thymus of mice not expressing the human Hox11 gene, and wherein the transgenic mouse is monitored for a change in the total number of thymocytes in the thymus of the transgenic mouse.

13. The method of claim 9 wherein the developmental and/or pathological condition is that the total number of T cells in the spleen and lymph nodes of the transgenic mouse is less than the total number of T cells in the spleen and lymph nodes mice not expressing the human Hox11 gene, and wherein the transgenic mouse is monitored for a change in the total number of T cells in the spleen and lymph nodes of the transgenic mouse.

* * * * *